(12) United States Patent
Takahashi

(10) Patent No.: US 7,968,157 B2
(45) Date of Patent: Jun. 28, 2011

(54) DISCOTIC NEMATIC MATERIAL, COMPOSITION, RETARDATION PLATE, ELLIPTICALLY-POLARIZING PLATE AND COMPOUND

(75) Inventor: Makoto Takahashi, Minami-ashigara (JP)

(73) Assignee: Fujifilm Corporation, Minato-ku, Tokyo (JP)

( * ) Notice: Subject to any disclaimer, the term of this patent is extended or adjusted under 35 U.S.C. 154(b) by 328 days.

(21) Appl. No.: 12/278,106

(22) PCT Filed: Feb. 6, 2007

(86) PCT No.: PCT/JP2007/052445
§ 371 (c)(1),
(2), (4) Date: Aug. 1, 2008

(87) PCT Pub. No.: WO2007/091701
PCT Pub. Date: Aug. 16, 2007

(65) Prior Publication Data
US 2009/0068378 A1      Mar. 12, 2009

(30) Foreign Application Priority Data
Feb. 6, 2006   (JP) .................................. 2006-028337

(51) Int. Cl.
C09K 19/34 (2006.01)
G02B 5/30 (2006.01)
C07D 285/08 (2006.01)
C07D 285/12 (2006.01)
C07D 271/06 (2006.01)
C07D 271/10 (2006.01)
G02F 1/1335 (2006.01)

(52) U.S. Cl. .................. 428/1.1; 428/1.31; 252/299.61; 548/128; 548/131; 548/136; 548/143; 349/117

(58) Field of Classification Search ............ 252/299.01, 252/299.61, 299.62; 428/1.1, 1.31; 548/128, 548/131, 136, 143; 349/117
See application file for complete search history.

(56) References Cited

U.S. PATENT DOCUMENTS
7,696,353 B2 * 4/2010 Takahashi et al. ............ 548/131
2008/0090027 A1 * 4/2008 Li et al. ........................ 428/1.31

FOREIGN PATENT DOCUMENTS
JP   2004-269424 A   9/2004
JP   2007-45806 A    2/2007

OTHER PUBLICATIONS

Rodrigo Cristiano et al., "Synthesis and characterization of low molecular mass luminescent liquid crystalline materials with 1,3,4-oxadiazole units", Liquid Crystals, vol. 32, No. 1, Jan. 2005, pp. 7-14.
Moriyuki Sato et al., "Thermotropic liquid crystalline polymers containing five-membered heterocyclic groups IX. Synthesis and optical properties of liquid crystalline semi-rigid polyesters composed of a quinquephenyl analogue containing 1,3,4-thiadiazole and aliphatic chains", Liquid Crystals, vol. 30, No. 9, Sep. 2003, pp. 1109-1114.
PCT/ISA/210.
PCT/ISA/237.
Notification Concerning Transmittal of International Preliminary Report on Patentability (Form PCT/IB/326), International Preliminary Report on Patentability (Form PCT/IB/373), Written Opinion of the International Search Authority (Form PCT/ISA/237) mailed in corresponding International Patent Application No. PCT/JP2007/052445, Aug. 12, 2008, The International Bureau of WIPO, Geneva, CH.

* cited by examiner

*Primary Examiner* — Shean C Wu
(74) *Attorney, Agent, or Firm* — Buchanan Ingersoll & Rooney PC

(57) ABSTRACT

A discotic nematic material comprising a compound of $R^1—H^1—Ar—H^2—R$ wherein Ar represents a substituted or unsubstituted aromatic hydrocarbon ring; $H^1$ and $H^2$ represent an aromatic hetero ring; and $R^1$ and $R^2$ represent a substituent having from 1 to 30 carbon atoms. The discotic nematic material contains a discotic liquid-crystal compound having a smaller number of side branches and capable of expressing an $N_D$ phase.

9 Claims, No Drawings

… … …

DISCOTIC NEMATIC MATERIAL, COMPOSITION, RETARDATION PLATE, ELLIPTICALLY-POLARIZING PLATE AND COMPOUND

TECHNICAL FIELD

The present invention relates to a discotic nematic material capable of expressing a discotic nematic phase and useful for formation of retardation plates, and to a composition containing the material. The invention also relates to a retardation plate having an optically-anisotropic layer formed with the composition, and to an elliptically-polarizing plate comprising it.

BACKGROUND ART

It is known that a discotic liquid-crystal compound, especially a liquid-crystal compound capable of expressing a discotic nematic phase (hereinafter referred to as "$N_D$ phase") is an extremely important compound as a material for optical compensatory films. Typical examples of a liquid-crystal compound are, for example, benzene derivatives, triphenylene derivatives, toluxene derivatives, phthalocyanine derivatives, as in a report by Destrade, et al. (see Molecular Crystals and Liquid Crystals, 1981, Vol. 71, p. 111), in which, in general, any of these derivatives forms a center mother nucleus of the molecule thereof and is substituted with radial side branches of a linear alkyl or alkoxy group or a substituted benzoyloxy group.

However, there are reported only limited cases relating to a liquid-crystal compound capable of expressing an $N_D$ phase (see THE CHEMICAL RECORD, 2002, Vol. 2, p. 59). For example, 2,3,6,7,10,11-hexa{4-(4-acryloyloxyhexyloxy)-benzoyloxy}triphenylene capable of expressing an $N_D$ phase within a broad temperature range is disclosed, and this has a mother nucleus of triphenylene that is substituted with 6 side branches. Almost all the other compounds are substituted with radial 6 side branches.

These days it is reported that a benzene compound, in which the benzene ring is substituted with three 1,3,4-oxadiazole substituents at the 1-, 3- and 5-positions thereof, expresses an $N_D$ phase (see Molecular Crystals and Liquid Crystals, 2001, Vol. 370, p. 391). However, no one knows a compound having less than 3 side branches and capable of expressing an $N_D$ phase.

As in the above, it has heretofore been considered that a compound having a larger number of side branches is more advantageous for expressing a discotic nematic phase.

A liquid-crystal compound capable of expressing an $N_D$ phase is useful, but has some problems in that conventional discotic liquid-crystal compounds have complicated structures and are difficult to produce and their costs are high.

DISCLOSURE OF THE INVENTION

An object of the invention is to provide a discotic nematic material that contains a discotic liquid-crystal compound having 2 side branches and capable of expressing an $N_D$ phase, which, however, could not be realized by any conventional discotic liquid-crystal compounds. Other objects of the invention are to provide a composition containing the material, and to provide a retardation plate and an elliptically-polarizing plate comprising the composition.

For attaining the objects, the invention provides the following:

(1) A discotic nematic material comprising a compound of the following formula (I):

$$R^1\text{—}H^1\text{—}Ar\text{—}H^2\text{—}R^2 \quad \text{Formula (I)}$$

wherein Ar represents a substituted or unsubstituted aromatic hydrocarbon ring; $H^1$ and $H^2$ each independently represents an aromatic hetero ring; and $R^1$ and $R^2$ each independently represents a substituent having from 1 to 30 carbon atoms.

(2) The discotic nematic material of (1), wherein $H^1$ and $H^2$ each independently represents a 1,2,4-oxadiazole ring, a 1,3,4-oxadiazole ring, a 1,2,4-thiadiazole ring or a 1,3,4-thiadiazole ring.

(3) The discotic nematic material of (2), wherein $H^1$ and $H^2$ each independently represents a 1,2,4-oxadiazole ring.

(4) The discotic nematic material of (1), wherein Ar is a substituted or unsubstituted benzene ring or a substituted or unsubstituted naphthalene ring.

(5) The discotic nematic material of (4), wherein Ar is a substituted or unsubstituted benzene ring.

(6) The discotic nematic material of (5), wherein the aromatic hetero ring of $H^1$ and $H^2$ bond to 1- and 3-positions of the substituted or unsubstituted benzene ring, respectively.

(7) The discotic nematic material of (1), wherein the compound of the formula (I) is represented by the following formula (II):

Formula (II)

wherein $Y^{11}$ and $Y^{12}$ each independently represents the following formula (II-A), (II-B) or (II-C):

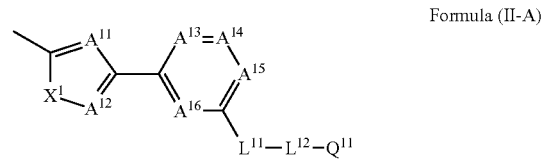

Formula (II-A)

wherein $A^{11}$, $A^{12}$, $A^{13}$, $A^{14}$, $A^{15}$ and $A^{16}$ each independently represents a methine group or a nitrogen atom; $X^1$ represents an oxygen atom, a sulfur atom, a methylene group or an imino group; $L^{11}$ represents —O—, —O—CO—, —CO—O—, —O—CO—O—, —S—, —NH—, —SO$_2$—, —CH$_2$—, —CH═CH— or —C≡C—, $L^{12}$ represents a divalent linking group selected from —O—, —S—, —C(═O)—, —SO$_2$—, —NH—, —CH$_2$—, —CH═CH— and —C≡C—, and their combinations, and when the group has a hydrogen atom, the hydrogen atom may be substituted with a substituent; $Q^{11}$ represents a polymerizable group or a hydrogen atom;

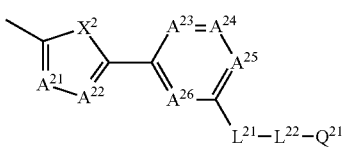

Formula (II-B)

wherein $A^{21}$, $A^{22}$, $A^{23}$, $A^{24}$, $A^{25}$ and $A^{26}$ each independently represents a methine group or a nitrogen atom; $X^2$ represents an oxygen atom, a sulfur atom, a methylene group or an imino group; $L^{21}$ represents —O—, —O—CO—, —CO—O—, —O—CO—O—, —S—, —NH—, —SO$_2$—, —CH$_2$—, —CH=CH— or —C≡C—, $L^{22}$ represents a divalent linking group selected from —O—, —S—, —C(=O)—, —SO$_2$—, —NH—, —CH$_2$—, —CH=CH— and —C≡C—, and their combinations, and when the group has a hydrogen atom, the hydrogen atom may be substituted with a substituent; $Q^{21}$ represents a polymerizable group or a hydrogen atom;

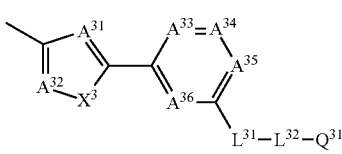

Formula (II-C)

wherein $A^{31}$, $A^{32}$, $A^{33}$, $A^{34}$, $A^{35}$ and $A^{36}$ each independently represents a methine group or a nitrogen atom; $X^3$ represents an oxygen atom, a sulfur atom, a methylene group or an imino group; $L^{31}$ represents —O—, —O—CO—, —CO—O—, —O—CO—O—, —S—, —NH—, —SO$_2$—, —CH$_2$—, —CH=CH— or —C≡C—, $L^{32}$ represents a divalent linking group selected from —O—, —S—, —C(=O)—, —SO$_2$—, —NH—, —CH$_2$—, —CH=CH— and —C≡C—, and their combinations, and when the group has a hydrogen atom, the hydrogen atom may be substituted with a substituent; $Q^{31}$ represents a polymerizable group or a hydrogen atom.

(8) A composition comprising a discotic nematic material of any one of (1) to (7).

(9) A retardation plate comprising at least one optically-anisotropic layer on a support, wherein the optically-anisotropic layer is formed with a composition of (8).

(10) An elliptically-polarizing plate comprising a retardation plate of (9) and a polarizing film.

(11) A liquid-crystal display device comprising a retardation plate of (9) or an elliptically-polarizing plate of (10).

(12) A compound of the following formula (III):

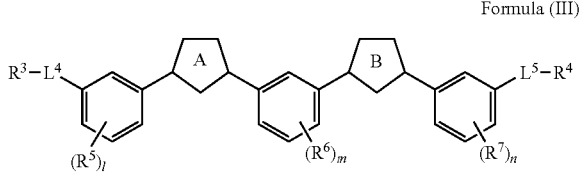

Formula (III)

wherein $R^3$ and $R^4$ each independently represents a linear or branched alkyl group having from 1 to 15 carbon atoms, an alkenyl group having from 2 to 15 carbon atoms, or an alkynyl group having from 2 to 15 carbon atoms, and the hydrogen atom in these groups may be substituted with a substituent; $R^5$, $R^6$ and $R^7$ each independently represents a substituent; l, m and n each independently indicates an integer of from 0 to 4; $L^4$ and $L^5$ each independently represents a single bond or a divalent linking group selected from —O—, —S—, —C(=O)—, —SO$_2$— and —NH— and their combinations; ring A and ring B each independently represents a 1,2,4-oxadiazole-3,5-diyl group, a 1,3,4-oxadiazole-2,5-diyl group, a 1,2,4-thiadiazole-3,5-diyl group, or a 1,3,4-thiadiazole-2,5-diyl group.

(13) The compound of (12), wherein the ring A and the ring A in formula (III) are a 1,2,4-oxadiazole-3,5-diyl group.

The invention has made it possible to provide an inexpensive discotic nematic material that contains a discotic liquid-crystal compound having a smaller number of side branches and capable of expressing an $N_D$ phase, which, however, could not be realized by any conventional discotic liquid-crystal compounds, and to provide a composition containing the material and a polarizer comprising the composition.

BEST MODE FOR CARRYING OUT THE INVENTION

The invention is described in detail hereinunder. In this description, the numerical range expressed by the wording "a number to another number" means the range that falls between the former number indicating the lowermost limit of the range and the latter number indicating the uppermost limit thereof. A liquid-crystal compound as referred to in this description is meant to indicate a compound having liquid crystallinity. In this description, a discotic nematic material means a material capable of forming a discotic nematic phase. In this description, a composition containing a discotic nematic material (this may be hereinafter simply referred to as "composition of the invention") may be under a condition under which it may lose or has lost its liquid crystallinity.

The material capable of expressing an $N_D$ phase of the invention is described in detail.

The discotic nematic material ($N_D$ material) of the invention contains a compound of the following formula (I). Though not specifically indicated, the hydrogen atom in the compound of formula (I) may be substituted with a substituent, not overstepping the spirit and the scope of the invention.

$$R^1\text{—}H^1\text{—Ar—}H^2\text{—}R^2 \qquad \text{Formula (I)}$$

wherein Ar represents a substituted or unsubstituted aromatic hydrocarbon ring; $H^1$ and $H^2$ represent an aromatic hetero ring; $R^1$ and $R^2$ represent a substituent having from 1 to 30 carbon atoms.

Ar is preferably a substituted or unsubstituted benzene ring or a substituted or unsubstituted naphthalene ring, more preferably a substituted or unsubstituted benzene ring, even more preferably an unsubstituted benzene ring.

Preferably, $H^1$ and $H^2$ each independently represents a 1,2,4-oxadiazole ring, a 1,3,4-oxadiazole ring, a 1,2,4-thiadiazole ring or a 1,3,4-thiadiazole ring, more preferably a 1,2,4-oxadiazole ring.

The bonding position of Ar to $H^1$ and $H^2$ is not specifically defined, not overstepping the spirit and the scope of the invention.

For example, when $H^1$ and $H^2$ each independently represents a 1,2,4-oxadiazole ring, a 1,3,4-oxadiazole ring, a 1,2,4-thiadiazole ring or a 1,3,4-thiadiazole ring, they may bond at the 3- or 5-position, and therefore may bond to Ar at any position thereof.

On the other hand, when Ar is a benzene ring, then $H^1$ and $H^2$ may bond to the benzene ring at any position thereof, but preferably bond at the 1- and 2-positions, or the 1- and 3-positions, or the 1- and 4-positions, more preferably at the 1- and 3-positions.

Preferred examples of the substituent that Ar may have are mentioned below.

The substituent includes a halogen atom (e.g., fluorine atom, chlorine atom, bromine atom, iodine atom), an alkyl group (preferably having from 1 to 30 carbon atoms, e.g., methyl group, ethyl group, n-propyl group, isopropyl group, tert-butyl group, n-octyl group, 2-ethylhexyl group), a cycloalkyl group (preferably having from 3 to 30 carbon atoms, e.g., cyclohexyl group, cyclopentyl group, 4-n-dodecylcyclohexyl group), a bicycloalkyl group (preferably having from 5 to 30 carbon atoms, or that is, a monovalent group derived from a bicycloalkane having from 5 to 30 carbon atoms by removing one hydrogen atom from it, e.g., bicyclo[1.2.2]heptan-2-yl group, bicyclo[2.2.2]octan-3-yl group), an alkenyl group (preferably having from 2 to 30 carbon atoms, e.g., vinyl group, allyl group), a cycloalkenyl group (preferably having from 3 to 30 carbon atoms, or that is, a monovalent group derived from a cycloalkene having from 3 to 30 carbon atoms by removing one hydrogen atom from it, e.g., 2-cyclopenten-1-yl group, 2-cyclohexen-1-yl group), a bicycloalkenyl group (preferably having from 5 to 30 carbon atoms, or that is, a monovalent group derived from a bicycloalkene having one double bond by removing one hydrogen atom from it, e.g., bicyclo[2.2.1]hept-2-en-1-yl group, bicyclo[2.2.2]oct-2-en-4-yl group), an alkynyl group (preferably having from 2 to 30 carbon atoms, e.g., ethynyl group, propargyl group), an aryl group (preferably having from 6 to 30 carbon atoms, e.g., phenyl group, p-tolyl group, naphthyl group), a heterocyclic group (preferably a monovalent group derived from a 5- or 6-membered, aromatic or non-aromatic heterocyclic compound by removing one hydrogen atom from it, more preferably a 5- or 6-membered aromatic heterocyclic group having from 3 to 30 carbon atoms, e.g., 2-furyl group, 2-thienyl group, 2-pyrimidinyl group, 2-benzothiazolyl group), a cyano group, a hydroxyl group, a nitro group, a carboxyl group, an alkoxy group (preferably having from 1 to 30 carbon atoms, e.g., methoxy group, ethoxy group, isopropoxy group, tert-butoxy group, n-octyloxy group, 2-methoxyethoxy group), an aryloxy group (preferably having from 6 to 30 carbon atoms, e.g., phenoxy group, 2-methylphenoxy group, 4-tert-butylphenoxy group, 3-nitrophenoxy group, 2-tetradecanoylaminophenoxy group), a silyloxy group (preferably having from 3 to 20 carbon atoms, e.g., trimethylsilyloxy group, tert-butyldimethylsilyloxy group), a heterocyclic-oxy group (preferably having from 2 to 30 carbon atoms, e.g., 1-phenyltetrazol-5-oxy group, 2-tetrahydropyranyloxy group), an acyloxy group (preferably a formyloxy group, or an alkylcarbonyloxy group having from 2 to 30 carbon atoms, or an arylcarbonyloxy group having from 6 to 30 carbon atoms, e.g., formyloxy group, acetyloxy group, pivaloyloxy group, stearoyloxy group, benzoyloxy group, p-methoxyphenylcarbonyloxy group), a carbamoyloxy group (preferably having from 1 to 30 carbon atoms, e.g., N,N-dimethylcarbamoyloxy group, N,N-diethylcarbamoyloxy group, morpholinocarbonyloxy group, N,N-di-n-octylaminocarbonyloxy group, N-n-octylcarbamoyloxy group), an alkoxycarbonyloxy group (preferably having from 2 to 30 carbon atoms, e.g., methoxycarbonyloxy group, ethoxycarbonyloxy group, tert-butoxycarbonyloxy group, n-octylcarbonyloxy group), an aryloxycarbonyloxy group (preferably having from 7 to 30 carbon atoms, e.g., phenoxycarbonyloxy group, p-methoxyphenoxycarbonyloxy group, p-n-hexadecyloxyphenoxycarbonyloxy group), an amino group (preferably an amino group, an alkylamino group having from 1 to 30 carbon atoms, an anilino group having from 6 to 30 carbon atoms, e.g., amino group, methylamino group, dimethylamino group, anilino group, N-methyl-anilino group, diphenylamino group), an acylamino group (preferably, a formylamino group, an alkylcarbonylamino group having from 1 to 30 carbon atoms, an arylcarbonylamino group having from 6 to 30 carbon atoms, e.g., formylamino group, acetylamino group, pivaloylamino group, lauroylamino group, benzoylamino group), an aminocarbonylamino group (preferably having from 1 to 30 carbon atoms, e.g., carbamoylamino group, N,N-dimethylaminocarbonylamino group, N,N-diethylaminocarbonylamino group, morpholinocarbonyl-amino group), an alkoxycarbonylamino group (preferably having from 2 to 30 carbon atoms, e.g., methoxycarbonyl-amino group, ethoxycarbonylamino group, tert-butoxycarbonylamino group, n-octadecyloxycarbonylamino group, N-methyl-methoxycarbonylamino group), an aryloxycarbonylamino group (preferably having from 7 to 30 carbon atoms, e.g., phenoxycarbonylamino group, p-chlorophenoxycarbonylamino group, m-n-octyloxyphenoxy-carbonylamino group), a sulfamoylamino group (preferably having from 0 to 30 carbon atoms, e.g., sulfamoylamino group, N,N-dimethylaminosulfonylamino group, N-n-octylaminosulfonylamino group), an alkyl or arylsulfonyl-amino group (preferably an alkylsulfonylamino group having from 1 to 30 carbon atoms, or an arylsulfonylamino group having from 6 to 30 carbon atoms, e.g., methylsulfonylamino group, butylsulfonylamino group, phenylsulfonylamino group, 2,3,5-trichlorophenylsulfonylamino group, p-methylsulfonyl-amino group), a mercapto group, an alkylthio group (preferably having from 1 to 30 carbon atoms, e.g., methylthio group, ethylthio group, n-hexadecylthio group), an arylthio group (preferably having from 6 to 30 carbon atoms, e.g., phenylthio group, p-chlorophenylthio group, m-methoxyphenyl group), a heterocyclic-thio group (preferably having from 2 to 30 carbon atoms, e.g., 2-benzothiazolylthio group, 1-phenyltetrazol-5-ylthio group), a sulfamoyl group (preferably having from 0 to 30 carbon atoms, e.g., N-ethylsulfamoyl group, N-(3-dodecyloxy-propyl)sulfamoyl group, N,N-dimethylsulfamoyl group, N-acetylsulfamoyl group, N-benzoylsulfamoyl group, N—(N'-phenylcarbamoyl)sulfamoyl group), a sulfo group, an alkyl or arylsulfinyl group (preferably an alkylsulfinyl group having from 1 to 30 carbon atoms, or an arylsulfinyl group having from 6 to 30 carbon atoms, e.g., methylsulfinyl group, ethylsulfinyl group, phenylsulfinyl group, p-methylphenylsulfinyl group), an alkyl or arylsulfonyl group (preferably an alkylsulfonyl group having from 1 to 30 carbon atoms, or an arylsulfonyl group having from 6 to 30 carbon atoms, e.g., methylsulfonyl group, ethylsulfonyl group, phenylsulfonyl group, p-methylphenylsulfonyl group), an acyl group (preferably a formyl group, an alkylcarbonyl group having from 2 to 30 carbon atoms, or an arylcarbonyl group having from 7 to 30 carbon atoms, e.g., acetyl group, pivaloyl group, benzoyl group), an aryloxycarbonyl group (preferably having from 7 to 30 carbon atoms, e.g., phenoxycarbonyl group, o-chlorophenoxycarbonyl group, m-nitrophenoxycarbonyl group, p-tert-butylphenoxycarbonyl group), an alkoxycarbonyl group (preferably having from 2 to 30 carbon atoms, e.g., methoxycarbonyl group, ethoxycarbonyl group, tert-butoxycarbonyl group, n-octadecyloxycarbonyl group), a carbamoyl group (preferably having from 1 to 30 carbon atoms, e.g., carbamoyl group, N-methylcarbamoyl group, N,N-dimethylcarbamoyl group, N,N-di-n-octylcarbamoyl group, N-(methylsulfonyl)carbamoyl group), an aryl or heterocyclic-azo group (preferably an arylazo group having from 6 to 30 carbon atoms, or a heterocyclic-azo group having from 3 to 30 carbon atoms, e.g., phenylazo group, p-chlorophenylazo group, 5-ethylthio-1,3,4-thiadiazol-2-ylazo group), an imido group (preferably N-succinimido group, N-phthalimido group), a phosphino group (preferably having from 2 to 30 carbon atoms, e.g., dimethylphosphino group, diphenylphosphino group, methylphenoxyphosphino group), a phosphinyl group (preferably having from 2 to 30 carbon atoms, e.g., phosphinyl group, dioctyloxyphosphinyl group, diethoxyphosphinyl group), a phosphinyloxy group (preferably having from 2 to 30 carbon atoms, e.g., diphenoxyphosphinyloxy group, dioctyloxyphosphinyloxy group), a phosphinylamino group (preferably having from 2 to 30 carbon atoms, e.g., dimethoxyphosphinylamino group, dimethylaminophosphinylamino group), a silyl group (preferably having from 3 to 30 carbon atoms, e.g., trimethylsilyl group, tert-butyldimethylsilyl group, phenyldimethylsilyl group).

In the above substituents having a hydrogen atom, the hydrogen atom may be removed and may be substituted with any of the above groups. Examples of the substituents of the type are an alkylcarbonylaminosulfonyl group, an arylcarbonylaminosulfonyl group, an alkylsulfonylamino-carbonyl group, an arylsulfonylaminocarbonyl group. Their concrete examples are a methylsulfonylaminocarbonyl group, a p-methylphenylsulfonylaminocarbonyl group, an acetyl-aminosulfonyl group, a benzoylaminosulfonyl group.

Of the above substituents, more preferred are an alkyl group, an alkoxy group, an alkoxycarbonyl group and an alkoxycarbonyloxy group having from 1 to 20 carbon atoms, and a cyano group and a halogen atom.

Examples of the substituent having from 1 to 30 carbon atoms for $R^1$ and $R^2$ may be the same as those mentioned above for the substituent that Ar may have, preferably an aryl group and a heterocyclic group (including those that are substituted).

The bonding position between $H^1$ and $R^1$ and between $H^2$ and $R^2$ is not specifically defined. For example, when $H^1$ and $H^2$ each independently represents a 1,2,4-oxadiazole ring, a 1,3,4-oxadiazole ring, a 1,2,4-thiadiazole ring or a 1,3,4-thiadiazole ring, they may bond at the 3- or 5-position, therefore preferably bonding to Ar at any of these positions and to $R^1$ or $R^2$ at the other position.

Preferred examples of the compound of formula (I) are those of the following formula (II):

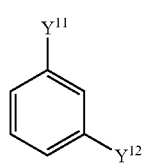

Formula (II)

wherein $Y^{11}$ and $Y^{12}$ each independently represents the following formula (II-A), (II-B) or (II-C).

In formula (II), the hydrogen atom on the benzene ring may be substituted with a substituent. Examples of the substituent in this case are an alkyl group, an alkoxy group, an aryloxy group, an acyl group, an alkoxycarbonyl group, an acyloxy group, an acylamino group, an alkoxycarbonylamino group, an alkylthio group, an arylthio group, a halogen atom, and a cyano group. Of those substituents, preferred are an alkyl group, an alkoxy group, an alkoxycarbonyl group, an acyloxy group, a halogen atom and a cyano group; more preferred are an alkyl group having from 1 to 12 carbon atoms, an alkoxy group having from 1 to 12 carbon atoms, an alkoxycarbonyl group having from 2 to 12 carbon atoms, an acyloxy group having from 2 to 12 carbon atoms, a halogen atom and a cyano group. More preferably, the benzene ring is unsubstituted.

$Y^{11}$ and $Y^{12}$ each independently represents the following formula (II-A), (II-B) or (II-C).

For smaller wavelength dispersion, preferred is formula (II-A) or (II-C), more preferred is formula (II-A). Preferably, $Y^{11}$ and $Y^{12}$ are the same.

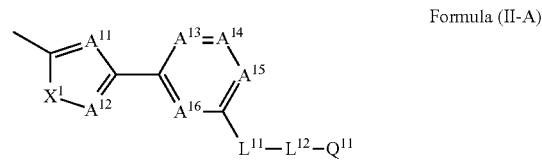

Formula (II-A)

wherein $A^{11}$, $A^{12}$, $A^{13}$, $A^{14}$, $A^{15}$ and $A^{16}$ each independently represents a methine group or a nitrogen atom; $X^1$ represents an oxygen atom, a sulfur atom, a methylene group or an imino group; $L^{11}$ represents —O—, —O—CO—, —CO—O—, —O—CO—O—, —S—, —NH—, —SO$_2$—, —CH$_2$—, —CH=CH— or —C≡C—; $L^{12}$ represents a divalent linking group selected from —O—, —S—, —C(=O)—, —SO$_2$—, —NH—, —CH$_2$—, —CH=CH— and —C≡C—, and their combinations, and when the group has a hydrogen atom, the hydrogen atom may be substituted with a substituent; $Q^{11}$ represents a polymerizable group or a hydrogen atom.

Preferably, at least one of $A^{11}$ and $A^{12}$ is a nitrogen atom; more preferably the two are both nitrogen atoms.

Preferably, at least three of $A^{13}$, $A^{14}$, $A^{15}$ and $A^{16}$ are methine groups; more preferably, all of them are methine groups; even more preferably the methine group is unsubstituted.

Examples of the substituent of the methine group for $A^{11}$, $A^{12}$, $A^{13}$, $A^{14}$, $A^{15}$ and $A^{16}$ are a halogen atom (fluorine atom, chlorine atom, bromine atom, iodine atom), a cyano group, a nitro group, an alkyl group having from 1 to 16 carbon atoms, an alkenyl group having from 2 to 16 carbon atoms, an alkynyl group having from 2 to 16 carbon atoms, a halogen-substituted alkyl group having from 1 to 16 carbon atoms, an alkoxy group having from 1 to 16 carbon atoms, an acyl group having from 2 to 16 carbon atoms, an alkylthio group having from 1 to 16 carbon atoms, an acyloxy group having from 2 to 16 carbon atoms, an alkoxycarbonyl group having from 2 to 16 carbon atoms, a carbamoyl group, an alkyl group-substituted carbamoyl group having from 2 to 16 carbon atoms, and an acylamino group having from 2 to 16 carbon atoms. Of those, preferred are a halogen atom, a cyano group, an alkyl group having from 1 to 6 carbon atoms, a halogen-substituted alkyl group having from 1 to 6 carbon atoms; more preferred are a halogen atom, an alkyl group having from 1 to 4 carbon atoms, a halogen-substituted alkyl group having from 1 to 4 carbon atoms; even more preferred are a halogen atom, an alkyl group having from 1 to 3 carbon atoms, a trifluoromethyl group.

$X^1$ represents an oxygen atom, a sulfur atom, a methylene group or an imino group, but is preferably an oxygen atom.

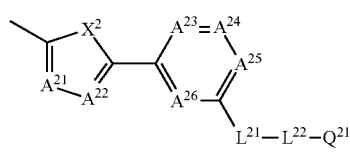

Formula (II-B)

wherein $A^{21}$, $A^{22}$, $A^{23}$, $A^{24}$, $A^{25}$ and $A^{26}$ each independently represents a methine group or a nitrogen atom; $X^2$ represents an oxygen atom, a sulfur atom, a methylene group or an imino group; $L^{21}$ represents —O—, —O—CO—, —CO—O—, —O—CO—O—, —S—, —NH—, —SO$_2$—, —CH$_2$—, —CH=CH— or —C≡C—; $L^{22}$ represents a divalent linking group selected from —O—, —S—, —C(=O)—, —SO$_2$—, —NH—, —CH$_2$—, —CH=CH— and —C≡C—, and their combinations, and when the group has a hydrogen atom, the hydrogen atom may be substituted with a substituent; $Q^{21}$ represents a polymerizable group or a hydrogen atom.

Preferably, at least one of $A^{21}$ and $A^{22}$ is a nitrogen atom; more preferably the two are both nitrogen atoms.

Preferably, at least three of $A^{23}$, $A^{24}$, $A^{25}$ and $A^{26}$ are methine groups; more preferably, all of them are methine groups; even more preferably the methine group is unsubstituted.

Examples of the substituent of the methine group for $A^{21}$, $A^{22}$, $A^{23}$, $A^{24}$, $A^{25}$ and $A^{26}$ are a halogen atom (fluorine atom, chlorine atom, bromine atom, iodine atom), a cyano group, a nitro group, an alkyl group having from 1 to 16 carbon atoms, an alkenyl group having from 2 to 16 carbon atoms, an alkynyl group having from 2 to 16 carbon atoms, a halogen-substituted alkyl group having from 1 to 16 carbon atoms, an alkoxy group having from 1 to 16 carbon atoms, an acyl group having from 2 to 16 carbon atoms, an alkylthio group having from 1 to 16 carbon atoms, an acyloxy group having from 2 to 16 carbon atoms, an alkoxycarbonyl group having from 2 to 16 carbon atoms, a carbamoyl group, an alkyl group-substituted carbamoyl group having from 2 to 16 carbon atoms, and an acylamino group having from 2 to 16 carbon atoms. Of those, preferred are a halogen atom, a cyano group, an alkyl group having from 1 to 6 carbon atoms, a halogen-substituted alkyl group having from 1 to 6 carbon atoms; more preferred are a halogen atom, an alkyl group having from 1 to 4 carbon atoms, a halogen-substituted alkyl group having from 1 to 4 carbon atoms; even more preferred are a halogen atom, an alkyl group having from 1 to 3 carbon atoms, a trifluoromethyl group.

$X^2$ represents an oxygen atom, a sulfur atom, a methylene group or an imino group, but is preferably an oxygen atom.

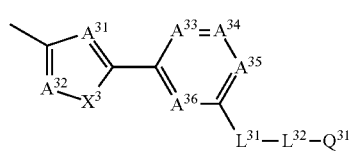

Formula (II-C)

wherein $A^{31}$, $A^{32}$, $A^{33}$, $A^{34}$, $A^{35}$ and $A^{36}$ each independently represents a methine group or a nitrogen atom; $X^3$ represents an oxygen atom, a sulfur atom, a methylene group or an imino group; $L^{31}$ represents —O—, —O—CO—, —CO—O—, —O—CO—O—, —S—, —NH—, —SO$_2$—, —CH$_2$—, —CH=CH— or —C≡C—; $L^{32}$ represents a divalent linking group selected from —O—, —S—, —C(=O)—, SO$_2$—, —NH—, —CH$_2$—, —CH=CH— and —C≡C—, and their combinations, and when the group has a hydrogen atom, the hydrogen atom may be substituted with a substituent; $Q^{31}$ represents a polymerizable group or a hydrogen atom;

Preferably, at least one of $A^{31}$ and $A^{32}$ is a nitrogen atom; more preferably the two are both nitrogen atoms.

Preferably, at least three of $A^{33}$, $A^{34}$, $A^{35}$ and $A^{36}$ are methine groups; more preferably, all of them are methine groups.

When $A^{31}$, $A^{32}$, $A^{33}$, $A^{34}$, $A^{35}$ and $A^{36}$ are methine groups, they may have a substituent. Examples of the substituent are a halogen atom (fluorine atom, chlorine atom, bromine atom, iodine atom), a cyano group, a nitro group, an alkyl group having from 1 to 16 carbon atoms, an alkenyl group having from 2 to 16 carbon atoms, an alkynyl group having from 2 to 16 carbon atoms, a halogen-substituted alkyl group having from 1 to 16 carbon atoms, an alkoxy group having from 1 to 16 carbon atoms, an acyl group having from 2 to 16 carbon atoms, an alkylthio group having from 1 to 16 carbon atoms, an acyloxy group having from 2 to 16 carbon atoms, an alkoxycarbonyl group having from 2 to 16 carbon atoms, a carbamoyl group, an alkyl group-substituted carbamoyl group having from 2 to 16 carbon atoms, and an acylamino group having from 2 to 16 carbon atoms. Of those, preferred are a halogen atom, a cyano group, an alkyl group having from 1 to 6 carbon atoms, a halogen-substituted alkyl group having from 1 to 6 carbon atoms; more preferred are a halogen atom, an alkyl group having from 1 to 4 carbon atoms, a halogen-substituted alkyl group having from 1 to 4 carbon atoms; even more preferred are a halogen atom, an alkyl group having from 1 to 3 carbon atoms, a trifluoromethyl group.

$X^3$ represents an oxygen atom, a sulfur atom, a methylene group or an imino group, but is preferably an oxygen atom.

$L^{11}$ in formula (II-A), $L^{21}$ in formula (II-B) and $L^{31}$ in formula (II-C) are preferably —O—, —O—CO—, —CO—O—, —O—CO—O—, —CH$_2$—, —CH=CH— or —C≡C—, more preferably —O—, —O—CO—, —CO—O—, —O—CO—O— or —CH$_2$—. When above group has a hydrogen atom, then the hydrogen atom may be substituted with a substituent. Preferred examples of the substituent are a halogen atom, a cyano group, a nitro group, an alkyl group having from 1 to 6 carbon atoms, a halogen atom-substituted alkyl group having from 1 to 6 carbon atoms, an alkoxy group having from 1 to 6 carbon atoms, an acyl group having from 2 to 6 carbon atoms, an alkylthio group having from 1 to 6 carbon atoms, an acyloxy group having from 2 to 6 carbon atoms, an alkoxycarbonyl group having from 2 to 6 carbon atoms, a carbamoyl group, an alkyl group-substituted carbamoyl group having from 2 to 6 carbon atoms, and an acylamino group having from 2 to 6 carbon atoms. Especially preferred are a halogen atom, and an alkyl group having from 1 to 6 carbon atoms.

$L^{12}$ in formula (II-A), $L^{22}$ in formula (II-B) and $L^{32}$ in formula (II-C) are preferably selected from —O—, —C(=O)—, —CH$_2$—, —CH=CH— and —C≡C—, and their combinations.

Preferably, $L^{12}$, $L^{22}$ and $L^{32}$ each independently has from 1 to 20 carbon atoms, more preferably from 2 to 14 carbon atoms. Even more preferably, they have from 1 to 16 (—CH$_2$—)'s and have from 2 to 14 carbon atoms, still more preferably they have from 2 to 12 (—CH$_2$—)'s and have from 2 to 14 carbon atoms, Especially preferably, $L^{12}$, $L^{22}$ and $L^{32}$ are independently selected from —O—, —S—, —C(=O)—, —SO$_2$—, —NH—, —CH$_2$—, —CH=CH— and —C≡C—, and their combinations, and have from 1 to 20 carbon atoms.

The hydrogen atom in —NH—, —CH$_2$— and —CH=CH— may be substituted with a substituent. Preferred examples of the substituent are a halogen atom, a cyano group, a nitro group, an alkyl group having from 1 to 6 carbon atoms, a halogen atom-substituted alkyl group having from 1 to 6 carbon atoms, an alkoxy group having from 1 to 6 carbon atoms, an acyl group having from 2 to 6 carbon atoms, an alkylthio group having from 1 to 6 carbon atoms, an acyloxy group having from 2 to 6 carbon atoms, an alkoxycarbonyl group having from 2 to 6 carbon atoms, a carbamoyl group, an alkyl group-substituted carbamoyl group having from 2 to 6 carbon atoms, and an acylamino group having from 2 to 6 carbon atoms. Especially preferred are a halogen atom, and an alkyl group having from 1 to 6 carbon atoms.

$Q^{11}$ in formula (II-A), $Q^{21}$ in formula (II-B) and $Q^{31}$ in formula (II-C) each independently represents a polymerizable group or a hydrogen atom.

In case where the $N_D$ material of the invention is used in optical films and the like such as optical compensatory films of which the retardation is desired not to change so much depending on heat applied thereto, then $Q^{11}$, $Q^{21}$ and $Q^{31}$ are preferably a polymerizable group.

The polymerization for the group is preferably addition polymerization (including ring-cleavage polymerization) or polycondensation. In other words, the polymerizable group is preferably a functional group that enables addition polymerization or polycondensation. Examples of the polymerizable group are shown below.

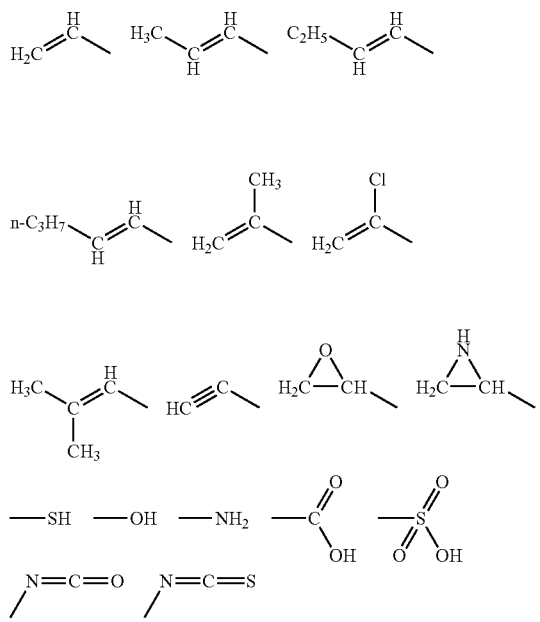

More preferably, the polymerizable group for $Q^{11}$, $Q^{21}$ and $Q^{31}$ is an addition-polymerizable functional group. The polymerizable group of the type is preferably a polymerizable ethylenic unsaturated group or a ring-cleavage polymerizable group.

Examples of the polymerizable ethylenic unsaturated group are the following (M-1) to (M-6):

(M-1)

(M-2)

(M-3)

(M-4)

(M-5)

(M-6)

In formulae (M-3) and (M-4), R represents a hydrogen atom or an alkyl group, preferably a hydrogen atom or a methyl group.

Of formulae (M-1) to (M-6), preferred are formulae (M-1) and (M-2), and more preferred is formula (M-1).

The ring-cleavage polymerizable group is preferably a cyclic ether group, more preferably an epoxy group or an oxetanyl group, most preferably an epoxy group.

The compounds of formula (II) are preferably those of the following formula (III):

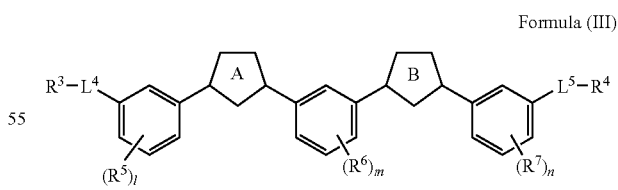
Formula (III)

wherein $R^3$ and $R^4$ each independently represents a linear or branched alkyl group having from 1 to 15 carbon atoms, an alkenyl group having from 2 to 15 carbon atoms, or an alkynyl group having from 2 to 15 carbon atoms, and the hydrogen atom in these groups may be substituted with a substituent; $R^5$, $R^6$ and $R^7$ each independently represents a substituent; l, m and n each independently indicates an integer of from 0 to 4; $L^4$ and $L^5$ each independently represents a single bond or a divalent linking group selected from —O—, —S—, —C(=O)—, —SO$_2$— and —NH— and their combinations; ring A and ring B each independently represents a 1,2,4-oxadiazole-3,5-diyl group, a 1,3,4-oxadiazole-2,5-diyl group, a 1,2,4-thiadiazole-3,5-diyl group, or a 1,3,4-thiadiazole-2,5-diyl group.

$R^3$ and $R^4$ are preferably a substituted or unsubstituted, linear or branched alkyl group having from 1 to 15 carbon atoms. Preferred examples of the substituent are a halogen atom, a cyano group, a nitro group, an alkyl group having from 1 to 6 carbon atoms, a halogen atom-substituted alkyl group having from 1 to 6 carbon atoms, an alkoxy group having from 1 to 6 carbon atoms, an acyl group having from 2 to 6 carbon atoms, an alkylthio group having from 1 to 6 carbon atoms, an acyloxy group having from 2 to 6 carbon atoms, an alkoxycarbonyl group having from 2 to 6 carbon atoms, a carbamoyl group, an alkyl group-substituted carbamoyl group having from 2 to 6 carbon atoms, an acylamino group having from 2 to 6 carbon atoms, and the above-mentioned polymerizable ethylenic unsaturated group; and more preferred are a halogen atom, an alkyl group having from 1 to 6 carbon atoms, and the above-mentioned polymerizable ethylenic unsaturated group.

Examples of the substituent for $R^5$, $R^6$ and $R^7$ include a halogen atom (fluorine atom, chlorine atom, bromine atom, iodine atom), a cyano group, a nitro group, an alkyl group having from 1 to 16 carbon atoms, an alkenyl group having from 2 to 16 carbon atoms, an alkynyl group having from 2 to 16 carbon atoms, a halogen atom-substituted alkyl group having from 1 to 16 carbon atoms, an alkoxy group having from 1 to 16 carbon atoms, an acyl group having from 2 to 16 carbon atoms, an alkylthio group having from 1 to 16 carbon atoms, an acyloxy group having from 2 to 16 carbon atoms, an alkoxycarbonyl group having from 2 to 16 carbon atoms, a carbamoyl group, an alkyl group-substituted carbamoyl group having from 2 to 16 carbon atoms, and an acylamino group having from 2 to 16 carbon atoms. Of those, preferred are a halogen atom, a cyano group, an alkyl group having from 1 to 6 carbon atoms, a halogen atom-substituted alkyl group having from 1 to 6 carbon atoms; more preferred are a halogen atom, an alkyl group having from 1 to 4 carbon atoms, a halogen atom-substituted alkyl group having from 1 to 4 carbon atoms; even more preferred are a halogen atom, an alkyl group having from 1 to 3 carbon atom, a trifluoromethyl group.

l, m and n are preferably 0, 1 or 2, more preferably 0 or 1, even more preferably 0. When l, m and n are 2 or more, then two or more $R^5$'s, $R^6$'s, and $R^7$'s may be the same or different.

$L^4$ and $L^5$ each independently represents a single bond or a divalent linking group selected from —O—, —S—, —C(=O)—, —SO$_2$— and —NH— and their combinations. The hydrogen atom in —NH— may be substituted with a substituent. Preferred examples of the substituent are a halogen atom, a cyano group, a nitro group, an alkyl group having from 1 to 6 carbon atoms, a halogen atom-substituted alkyl group having from 1 to 6 carbon atoms, an alkoxy group having from 1 to 6 carbon atoms, an acyl group having from 2 to 6 carbon atoms, an alkylthio group having from 1 to 6 carbon atoms, an acyloxy group having from 2 to 6 carbon atoms, an alkoxycarbonyl group having from 2 to 6 carbon atoms, a carbamoyl group, an alkyl group-substituted carbamoyl group having from 2 to 6 carbon atoms, and an acylamino group having from 2 to 6 carbon atoms; more preferred are a halogen atom, an alkyl group having from 1 to 6 carbon atoms. $L^4$ and $L^5$ are preferably a single bond, —O—, —O—CO—, —CO—O—, —O—CO—O—, more preferably —CO—O—.

Ring A and ring B are preferably a 1,2,4-oxadiazole-3,5-diyl group.

Specific examples of the compounds of formula (I) are mentioned below, to which, however, the invention should not be limited.

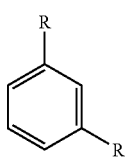 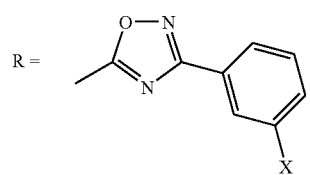

| X = | | |
|---|---|---|
| —OC$_4$H$_9$ | | D-1 |
| —OC$_5$H$_{11}$ | | D-2 |
| —OC$_6$H$_{13}$ | | D-3 |
| —OC$_7$H$_{15}$ | | D-4 |
| —OC$_8$H$_{17}$ | | D-5 |
| —OCH$_2$CH(CH$_3$)C$_4$H$_9$ | | D-6 |
| —O(CH$_2$)$_2$OCOCH=CH$_2$ | | D-7 |
| —O(CH$_2$)$_3$OCOCH=CH$_2$ | | D-8 |
| —O(CH$_2$)$_4$OCOCH=CH$_2$ | | D-9 |
| —O(CH$_2$)$_5$OCOCH=CH$_2$ | | D-10 |

-continued

| | |
|---|---|
| —O(CH₂)₆OCOCH=CH₂ | D-11 |
| —O(CH₂)₇OCOCH=CH₂ | D-12 |
| —O(CH₂)₈OCOCH=CH₂ | D-13 |
| —O(CH₂)₂CH(CH₃)OCOCH=CH₂ | D-14 |
| —O(CH₂)₃CH(CH₃)OCOCH=CH₂ | D-15 |
| —O(CH₂CH₂O)₂COCH=CH₂ | D-16 |
| —O(CH₂)₄OCOC(CH₃)=CH₂ | D-17 |
| —O(CH₂)₄OCOCH=CHCH₃ | D-18 |
| —O(CH₂)₄OCH=CH₂ | D-19 |
| —O(CH₂)₄—CH—CH₂ (epoxide) | D-20 |

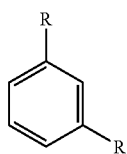 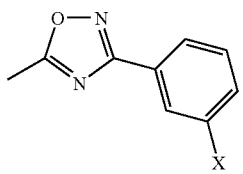

| X = | | |
|---|---|---|
| —OCOC₄H₉ | D-21 |
| —OCOC₅H₁₁ | D-22 |
| —OCOC₆H₁₃ | D-23 |
| —OCO(CH₂)₂OCOCH=CH₂ | D-24 |
| —OCO(CH₂)₃OCOCH=CH₂ | D-25 |
| —OCO(CH₂)₄OCOCH=CH₂ | D-26 |
| —OCO(CH₂)₅OCOCH=CH₂ | D-27 |
| —OCO(CH₂)₆OCOCH=CH₂ | D-28 |
| —OCO(CH₂)₇OCOCH=CH₂ | D-29 |
| —OCO(CH₂)₂CH(CH₃)OCOCH=CH₂ | D-30 |
| —OCO(CH₂)₂OCOC(CH₃)=CH₂ | D-31 |
| —OCO(CH₂)₂OCOCH=CHCH₃ | D-32 |
| —OCO(CH₂)₄OCH=CH₂ | D-33 |
| —OCO(CH₂)₄—CH—CH₂ (epoxide) | D-34 |

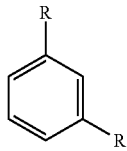 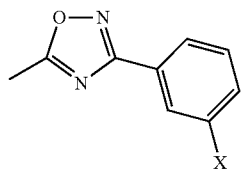

| X = | | |
|---|---|---|
| | —OCOOC₄H₉ | D-35 |
| | —OCOOC₅H₁₁ | D-36 |
| | —OCOOC₆H₁₃ | D-37 |
| | —OCOO(CH₂)₂OCOCH=CH₂ | D-38 |
| | —OCOO(CH₂)₃OCOCH=CH₂ | D-39 |
| | —OCOO(CH₂)₄OCOCH=CH₂ | D-40 |
| | —OCOO(CH₂)₅OCOCH=CH₂ | D-41 |
| | —OCOO(CH₂)₆OCOCH=CH₂ | D-42 |
| | —OCOO(CH₂)₇OCOCH=CH₂ | D-43 |
| | —OCOOCH(CH₃)CH₂CH₂OCOCH=CH₂ | D-44 |
| | —OCOO(CH₂CH₂O)₂COCH=CH₂ | D-45 |
| | —OCOO(CH₂)₂OCOC(CH₃)=CH₂ | D-46 |
| | —OCOO(CH₂)₂OCOCH=CHCH₃ | D-47 |
| | —OCOO(CH₂)₄OCH=CH₂ | D-48 |
| | —OCOO(CH₂)₄—CH—CH₂ (epoxide) | D-49 |

$$X_i = c_i / q_{max}$$

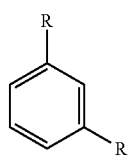 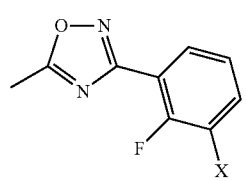

| X = | | |
|---|---|---|
| | —OC₆H₁₃ | D-50 |
| | —OCOC₅H₁₁ | D-51 |
| | —OCOOC₄H₉ | D-52 |
| | —O(CH₂)₄OCOCH=CH₂ | D-53 |
| | —O(CH₂)₆OCOCH=CH₂ | D-54 |
| | —OCO(CH₂)₃OCOCH=CH₂ | D-55 |
| | —OCO(CH₂)₄OCOCH=CH₂ | D-56 |
| | —OCOO(CH₂)₂OCOCH=CH₂ | D-57 |
| | —OCOO(CH₂)₄OCOCH=CH₂ | D-58 |
| | —O(CH₂)₂OCOC(CH₃)=CH₂ | D-59 |
| | —O(CH₂)₂OCOCH=CHCH₃ | D-60 |
| | —O(CH₂)₄OCH=CH₂ | D-61 |
| | —O(CH₂)₄—CH—CH₂ (epoxide) | D-62 |

-continued

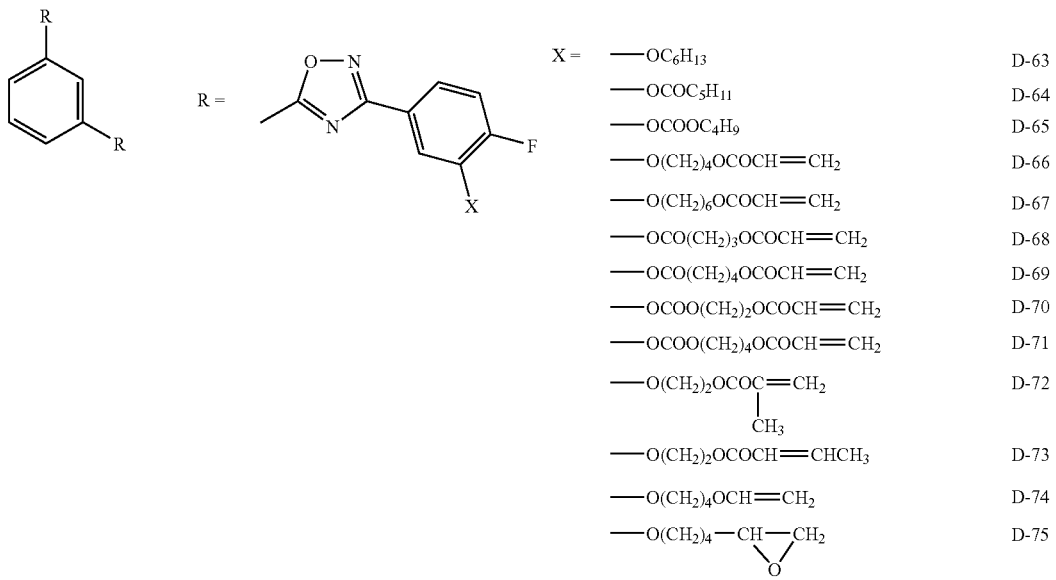

| X = | | |
|---|---|---|
| —OC₆H₁₃ | | D-63 |
| —OCOC₅H₁₁ | | D-64 |
| —OCOOC₄H₉ | | D-65 |
| —O(CH₂)₄OCOCH═CH₂ | | D-66 |
| —O(CH₂)₆OCOCH═CH₂ | | D-67 |
| —OCO(CH₂)₃OCOCH═CH₂ | | D-68 |
| —OCO(CH₂)₄OCOCH═CH₂ | | D-69 |
| —OCOO(CH₂)₂OCOCH═CH₂ | | D-70 |
| —OCOO(CH₂)₄OCOCH═CH₂ | | D-71 |
| —O(CH₂)₂OCOC(CH₃)═CH₂ | | D-72 |
| —O(CH₂)₂OCOCH═CHCH₃ | | D-73 |
| —O(CH₂)₄OCH═CH₂ | | D-74 |
| —O(CH₂)₄—CH—CH₂ (epoxide) | | D-75 |

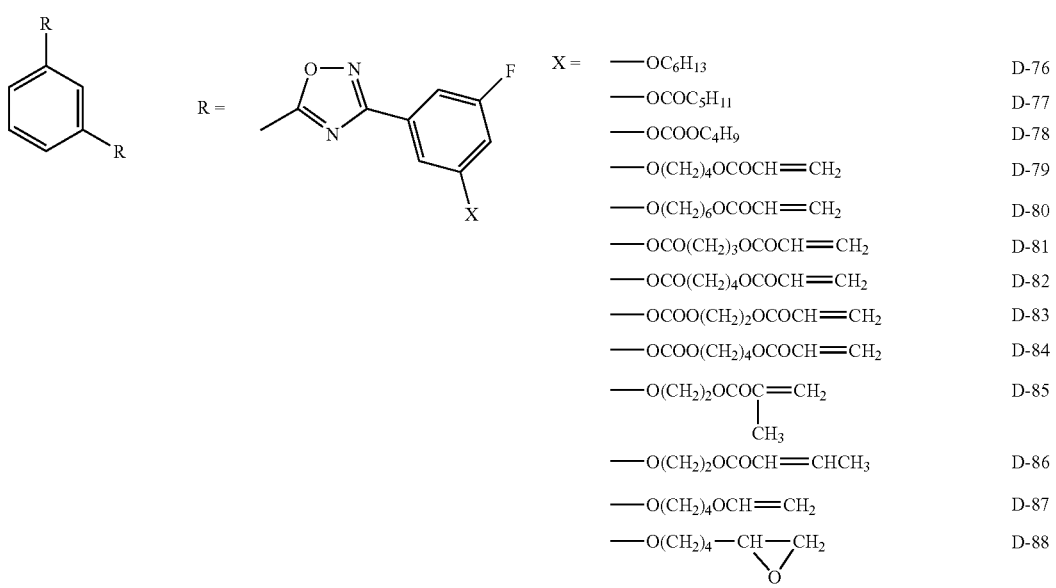

| X = | | |
|---|---|---|
| —OC₆H₁₃ | | D-76 |
| —OCOC₅H₁₁ | | D-77 |
| —OCOOC₄H₉ | | D-78 |
| —O(CH₂)₄OCOCH═CH₂ | | D-79 |
| —O(CH₂)₆OCOCH═CH₂ | | D-80 |
| —OCO(CH₂)₃OCOCH═CH₂ | | D-81 |
| —OCO(CH₂)₄OCOCH═CH₂ | | D-82 |
| —OCOO(CH₂)₂OCOCH═CH₂ | | D-83 |
| —OCOO(CH₂)₄OCOCH═CH₂ | | D-84 |
| —O(CH₂)₂OCOC(CH₃)═CH₂ | | D-85 |
| —O(CH₂)₂OCOCH═CHCH₃ | | D-86 |
| —O(CH₂)₄OCH═CH₂ | | D-87 |
| —O(CH₂)₄—CH—CH₂ (epoxide) | | D-88 |

-continued

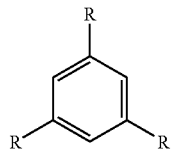 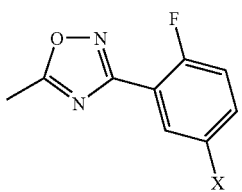

| X = | | |
|---|---|---|
| | —OC$_6$H$_{13}$ | D-89 |
| | —OCOC$_5$H$_{11}$ | D-90 |
| | —OCOOC$_4$H$_9$ | D-91 |
| | —O(CH$_2$)$_4$OCOCH=CH$_2$ | D-92 |
| | —O(CH$_2$)$_6$OCOCH=CH$_2$ | D-93 |
| | —OCO(CH$_2$)$_3$OCOCH=CH$_2$ | D-94 |
| | —OCO(CH$_2$)$_4$OCOCH=CH$_2$ | D-95 |
| | —OCOO(CH$_2$)$_2$OCOCH=CH$_2$ | D-96 |
| | —OCOO(CH$_2$)$_4$OCOCH=CH$_2$ | D-97 |
| | —O(CH$_2$)$_2$OCOC(CH$_3$)=CH$_2$ | D-98 |
| | —O(CH$_2$)$_2$OCOCH=CHCH$_3$ | D-99 |
| | —O(CH$_2$)$_4$OCH=CH$_2$ | D-100 |
| | —O(CH$_2$)$_4$—CH—CH$_2$ (epoxide) | D-101 |

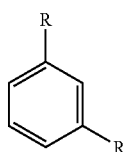 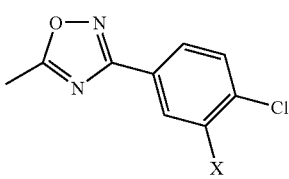

| X = | | |
|---|---|---|
| | —OC$_6$H$_{13}$ | D-102 |
| | —OCOC$_5$H$_{11}$ | D-103 |
| | —OCOOC$_4$H$_9$ | D-104 |
| | —O(CH$_2$)$_4$OCOCH=CH$_2$ | D-105 |
| | —O(CH$_2$)$_6$OCOCH=CH$_2$ | D-106 |
| | —OCO(CH$_2$)$_3$OCOCH=CH$_2$ | D-107 |
| | —OCO(CH$_2$)$_4$OCOCH=CH$_2$ | D-108 |
| | —OCOO(CH$_2$)$_2$OCOCH=CH$_2$ | D-109 |
| | —OCOO(CH$_2$)$_4$OCOCH=CH$_2$ | D-110 |
| | —O(CH$_2$)$_2$OCOC(CH$_3$)=CH$_2$ | D-111 |
| | —O(CH$_2$)$_2$OCOCH=CHCH$_3$ | D-112 |
| | —O(CH$_2$)$_4$OCH=CH$_2$ | D-113 |
| | —O(CH$_2$)$_4$—CH—CH$_2$ (epoxide) | D-114 |

-continued

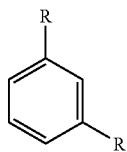 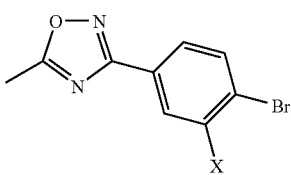

| X = | |
|---|---|
| —OC$_6$H$_{13}$ | D-115 |
| —OCOC$_5$H$_{11}$ | D-116 |
| —OCOOC$_4$H$_9$ | D-117 |
| —O(CH$_2$)$_4$OCOCH=CH$_2$ | D-118 |
| —O(CH$_2$)$_6$OCOCH=CH$_2$ | D-119 |
| —OCO(CH$_2$)$_3$OCOCH=CH$_2$ | D-120 |
| —OCO(CH$_2$)$_4$OCOCH=CH$_2$ | D-121 |
| —OCOO(CH$_2$)$_2$OCOCH=CH$_2$ | D-122 |
| —OCOO(CH$_2$)$_4$OCOCH=CH$_2$ | D-123 |
| —O(CH$_2$)$_2$OCOC(CH$_3$)=CH$_2$ | D-124 |
| —O(CH$_2$)$_2$OCOCH=CHCH$_3$ | D-125 |
| —O(CH$_2$)$_4$OCH=CH$_2$ | D-126 |
| —O(CH$_2$)$_4$—CH—CH$_2$ (epoxide) | D-127 |

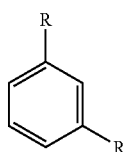 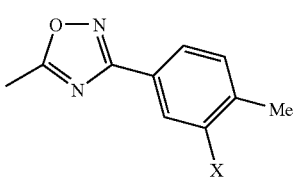

| X = | |
|---|---|
| —OC$_6$H$_{13}$ | D-128 |
| —OCOC$_5$H$_{11}$ | D-129 |
| —OCOOC$_4$H$_9$ | D-130 |
| —O(CH$_2$)$_4$OCOCH=CH$_2$ | D-131 |
| —O(CH$_2$)$_6$OCOCH=CH$_2$ | D-132 |
| —OCO(CH$_2$)$_3$OCOCH=CH$_2$ | D-133 |
| —OCO(CH$_2$)$_4$OCOCH=CH$_2$ | D-134 |
| —OCOO(CH$_2$)$_2$OCOCH=CH$_2$ | D-135 |
| —OCOO(CH$_2$)$_4$OCOCH=CH$_2$ | D-136 |
| —O(CH$_2$)$_2$OCOC(CH$_3$)=CH$_2$ | D-137 |
| —O(CH$_2$)$_2$OCOCH=CHCH$_3$ | D-138 |
| —O(CH$_2$)$_4$OCH=CH$_2$ | D-139 |
| —O(CH$_2$)$_4$—CH—CH$_2$ (epoxide) | D-140 |

-continued

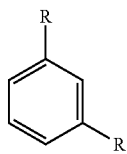 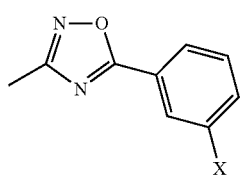

| X = | | |
|---|---|---|
| | —OC$_6$H$_{13}$ | D-141 |
| | —OCOC$_5$H$_{11}$ | D-142 |
| | —OCOOC$_4$H$_9$ | D-143 |
| | —O(CH$_2$)$_4$OCOCH=CH$_2$ | D-144 |
| | —O(CH$_2$)$_6$OCOCH=CH$_2$ | D-145 |
| | —OCO(CH$_2$)$_3$OCOCH=CH$_2$ | D-146 |
| | —OCO(CH$_2$)$_4$OCOCH=CH$_2$ | D-147 |
| | —OCOO(CH$_2$)$_2$OCOCH=CH$_2$ | D-148 |
| | —OCOO(CH$_2$)$_4$OCOCH=CH$_2$ | D-149 |
| | —O(CH$_2$)$_2$OCOC(CH$_3$)=CH$_2$ | D-150 |
| | —O(CH$_2$)$_2$OCOCH=CHCH$_3$ | D-151 |
| | —O(CH$_2$)$_4$OCH=CH$_2$ | D-152 |
| | —O(CH$_2$)$_4$—CH—CH$_2$ (epoxide) | D-153 |

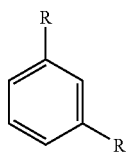 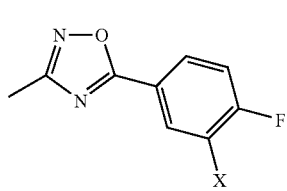

| X = | | |
|---|---|---|
| | —OC$_6$H$_{13}$ | D-154 |
| | —OCOC$_5$H$_{11}$ | D-155 |
| | —OCOOC$_4$H$_9$ | D-156 |
| | —O(CH$_2$)$_4$OCOCH=CH$_2$ | D-157 |
| | —O(CH$_2$)$_6$OCOCH=CH$_2$ | D-158 |
| | —OCO(CH$_2$)$_3$OCOCH=CH$_2$ | D-159 |
| | —OCO(CH$_2$)$_4$OCOCH=CH$_2$ | D-160 |
| | —OCOO(CH$_2$)$_2$OCOCH=CH$_2$ | D-161 |
| | —OCOO(CH$_2$)$_4$OCOCH=CH$_2$ | D-162 |
| | —O(CH$_2$)$_2$OCOC(CH$_3$)=CH$_2$ | D-163 |
| | —O(CH$_2$)$_2$OCOCH=CHCH$_3$ | D-164 |
| | —O(CH$_2$)$_4$OCH=CH$_2$ | D-165 |
| | —O(CH$_2$)$_4$—CH—CH$_2$ (epoxide) | D-166 |

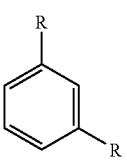 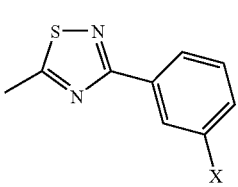

| X = | —O(CH$_2$)$_4$OCOCH=CH$_2$ | D-167 |
|---|---|---|

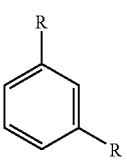 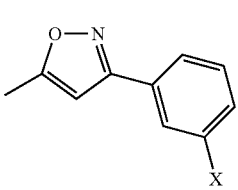

| X = | —O(CH$_2$)$_4$OCOCH=CH$_2$ | D-168 |
|---|---|---|

-continued
| | | | |
|---|---|---|---|
| 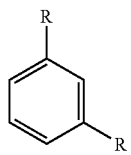 | R = 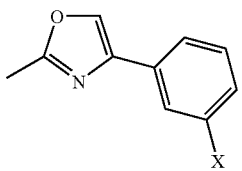 | X = —O(CH$_2$)$_4$OCOCH=CH$_2$ | D-169 |
| 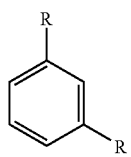 | R = 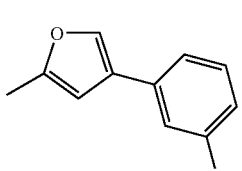 | X = —O(CH$_2$)$_4$OCOCH=CH$_2$ | D-170 |
| 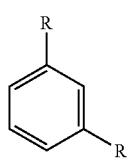 | R = 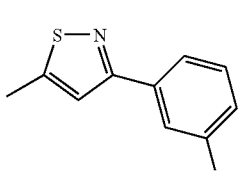 | X = —O(CH$_2$)$_4$OCOCH=CH$_2$ | D-171 |
| 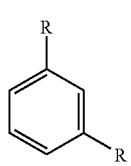 | R = 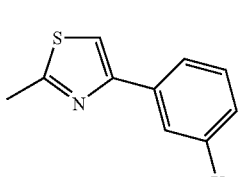 | X = —O(CH$_2$)$_4$OCOCH=CH$_2$ | D-172 |
| 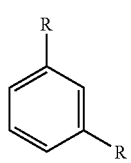 | R = 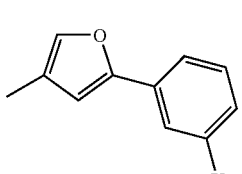 | X = —O(CH$_2$)$_4$OCOCH=CH$_2$ | D-173 |
| 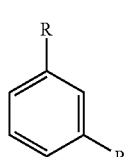 | R = 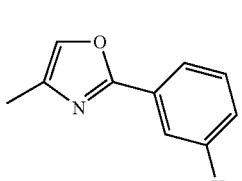 | X = —O(CH$_2$)$_4$OCOCH=CH$_2$ | D-174 |

| | | | |
|---|---|---|---|
| 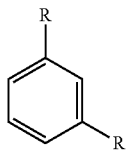 R = | 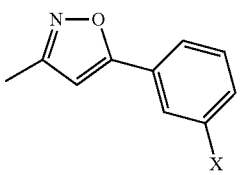 | X = —O(CH$_2$)$_4$OCOCH=CH$_2$ | D-175 |
| 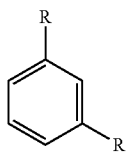 R = | 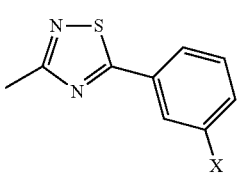 | X = —O(CH$_2$)$_4$OCOCH=CH$_2$ | D-176 |
| 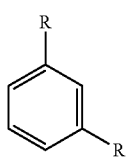 R = | 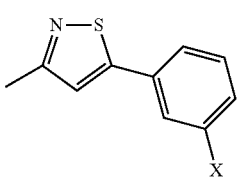 | X = —O(CH$_2$)$_4$OCOCH=CH$_2$ | D-177 |
| 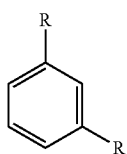 R = | 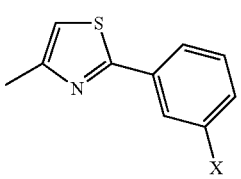 | X = —O(CH$_2$)$_4$OCOCH=CH$_2$ | D-178 |
| 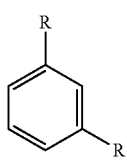 R = | 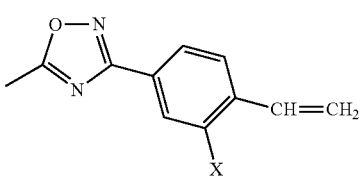 | X = —O(CH$_2$)$_3$OCOCH=CH$_2$ | D-179 |
| 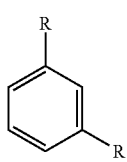 R = |  | X = —O(CH$_2$)$_4$OCOCH=CH$_2$ | D-180 |

-continued
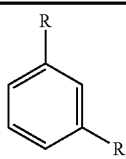 R = 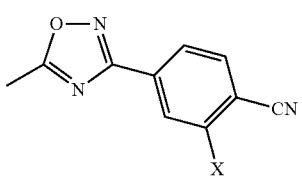 X = —O(CH₂)₅OCOCH=CH₂  D-181
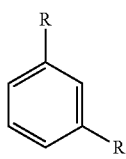 R = 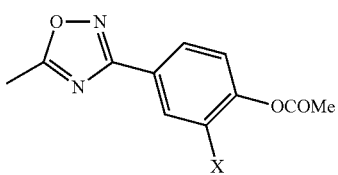 X = —O(CH₂)₆OCOCH=CH₂  D-182
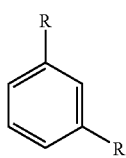 R = 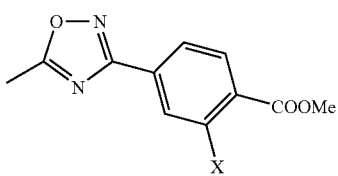 X = —O(CH₂)₅OCOCH=CH₂  D-183
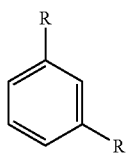 R = 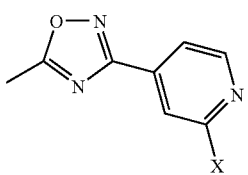 X = —O(CH₂)₃OCOCH=CH₂  D-184
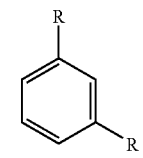 R = 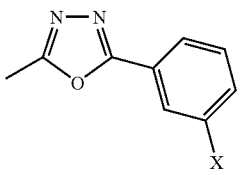
| X = | | |
|---|---|---|
| | —OC₆H₁₃ | D-185 |
| | —OCOC₅H₁₁ | D-186 |
| | —OCOOC₄H₉ | D-187 |
| | —O(CH₂)₄OCOCH=CH₂ | D-188 |
| | —O(CH₂)₆OCOCH=CH₂ | D-189 |
| | —OCO(CH₂)₃OCOCH=CH₂ | D-190 |
| | —OCO(CH₂)₄OCOCH=CH₂ | D-191 |
| | —OCOO(CH₂)₂OCOCH=CH₂ | D-192 |
| | —OCOO(CH₂)₄OCOCH=CH₂ | D-193 |
| | —O(CH₂)₂OCOC(CH₃)=CH₂ | D-194 |
| | —O(CH₂)₂OCOCH=CHCH₃ | D-195 |
| | —O(CH₂)₄OCH=CH₂ | D-196 |
| | —O(CH₂)₄—CH—CH₂ (epoxide) | D-197 |

-continued

| | | X = | | |
|---|---|---|---|---|
| 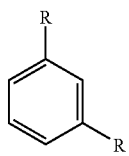 | 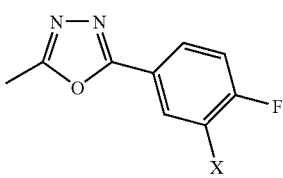 | —OC$_6$H$_{13}$ | D-198 |
| | | —OCOC$_5$H$_{11}$ | D-199 |
| | | —OCOOC$_4$H$_9$ | D-200 |
| | | —O(CH$_2$)$_4$OCOCH=CH$_2$ | D-201 |
| | | —O(CH$_2$)$_6$OCOCH=CH$_2$ | D-202 |
| | | —OCO(CH$_2$)$_3$OCOCH=CH$_2$ | D-203 |
| | | —OCO(CH$_2$)$_4$OCOCH=CH$_2$ | D-204 |
| | | —OCOO(CH$_2$)$_2$OCOCH=CH$_2$ | D-205 |
| | | —OCOO(CH$_2$)$_4$OCOCH=CH$_2$ | D-206 |
| | | —O(CH$_2$)$_2$OCOC(CH$_3$)=CH$_2$ | D-207 |
| | | —O(CH$_2$)$_2$OCOCH=CHCH$_3$ | D-208 |
| | | —O(CH$_2$)$_4$OCH=CH$_2$ | D-209 |
| | | —O(CH$_2$)$_4$—CH—CH$_2$ (epoxide) | D-210 |

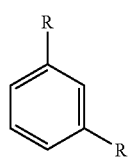 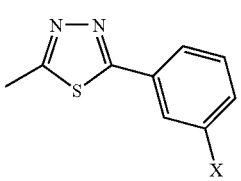 X = —O(CH$_2$)$_4$OCOCH=CH$_2$    D-211

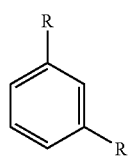 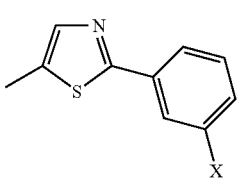 X = —O(CH$_2$)$_4$OCOCH=CH$_2$    D-212

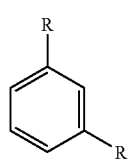 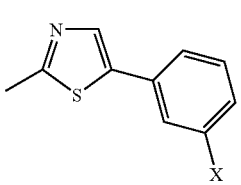 X = —O(CH$_2$)$_4$OCOCH=CH$_2$    D-213

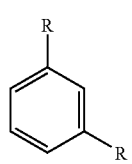 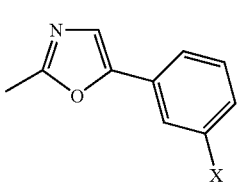 X = —O(CH$_2$)$_4$OCOCH=CH$_2$    D-214

-continued

| R group (phenyl with two R substituents) | R = | X = | No. |
|---|---|---|---|
| 1,3-phenyl | 5-methyl-2-(3-X-phenyl)oxazole | —O(CH$_2$)$_4$OCOCH=CH$_2$ | D-215 |
| 1,3-phenyl | 5-methyl-2-(3-X-phenyl)furan | —O(CH$_2$)$_4$OCOCH=CH$_2$ | D-216 |
| 1,3-phenyl | 5-methyl-2-(3-X-phenyl)thiophene | —O(CH$_2$)$_4$OCOCH=CH$_2$ | D-217 |

For R = 5-methyl-3-(3-X-phenyl)-1,2,4-oxadiazole (1,3-phenyl core):

| X = | No. |
|---|---|
| —COOC$_4$H$_9$ | D-218 |
| —COOC$_5$H$_{11}$ | D-219 |
| —COOC$_6$H$_{13}$ | D-220 |
| —COO(CH$_2$)$_2$OCOCH=CH$_2$ | D-221 |
| —COO(CH$_2$)$_3$OCOCH=CH$_2$ | D-222 |
| —COO(CH$_2$)$_4$OCOCH=CH$_2$ | D-223 |
| —COO(CH$_2$)$_5$OCOCH=CH$_2$ | D-224 |
| —COO(CH$_2$)$_6$OCOCH=CH$_2$ | D-225 |
| —COO(CH$_2$)$_7$OCOCH=CH$_2$ | D-226 |
| —COO(CH$_2$)$_8$OCOCH=CH$_2$ | D-227 |
| —COO(CH$_2$CH$_2$O)$_2$COCH=CH$_2$ | D-228 |
| —COO(CH$_2$)$_2$CH(CH$_3$)OCOCH=CH$_2$ | D-229 |
| —COO(CH$_2$)$_3$CH(CH$_3$)OCOCH=CH$_2$ | D-230 |
| —COO(CH$_2$)$_4$CH(CH$_3$)OCOCH=CH$_2$ | D-231 |
| —COOCH$_2$CH(CH$_3$)CH$_2$OCOCH=CH$_2$ | D-232 |
| —COO(CH$_2$)$_2$CH(CH$_3$)(CH$_2$)$_2$OCOCH=CH$_2$ | D-233 |
| —COOCH(CH$_3$)(CH$_2$)$_2$OCOCH=CH$_2$ | D-234 |
| —COO(CH$_2$)$_5$OCOC(CH$_3$)=CH$_2$ | D-235 |
| —COO(CH$_2$)$_4$OCH=CH$_2$ | D-236 |
| —COO(CH$_2$)$_4$—CH(—O—)CH$_2$ (glycidyl) | D-237 |

-continued

| | | | |
|---|---|---|---|
| 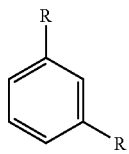 | R = 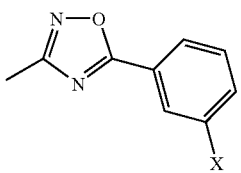 | X = —COOC$_4$H$_9$ | D-238 |
| | | —COOC$_5$H$_{11}$ | D-239 |
| | | —COOC$_6$H$_{13}$ | D-240 |
| | | —COO(CH$_2$)$_2$OCOCH=CH$_2$ | D-241 |
| | | —COO(CH$_2$)$_3$OCOCH=CH$_2$ | D-242 |
| | | —COO(CH$_2$)$_4$OCOCH=CH$_2$ | D-243 |
| | | —COO(CH$_2$)$_5$OCOCH=CH$_2$ | D-244 |
| | | —COO(CH$_2$)$_6$OCOCH=CH$_2$ | D-245 |
| | | —COO(CH$_2$)$_7$OCOCH=CH$_2$ | D-246 |
| | | —COO(CH$_2$)$_8$OCOCH=CH$_2$ | D-247 |
| | | —COO(CH$_2$CH$_2$O)$_2$COCH=CH$_2$ | D-248 |
| | | —COO(CH$_2$)$_2$CH(CH$_3$)OCOCH=CH$_2$ | D-249 |
| | | —COO(CH$_2$)$_3$CH(CH$_3$)OCOCH=CH$_2$ | D-250 |
| | | —COO(CH$_2$)$_4$CH(CH$_3$)OCOCH=CH$_2$ | D-251 |
| | | —COOCH$_2$CH(CH$_3$)CH$_2$OCOCH=CH$_2$ | D-252 |
| | | —COO(CH$_2$)$_2$CH(CH$_3$)(CH$_2$)$_2$OCOCH=CH$_2$ | D-253 |
| | | —COOCH(CH$_3$)(CH$_2$)$_2$OCOCH=CH$_2$ | D-254 |
| | | —COO(CH$_2$)$_5$OCOC(CH$_3$)=CH$_2$ | D-255 |
| | | —COO(CH$_2$)$_4$OCH=CH$_2$ | D-256 |
| | | —COO(CH$_2$)$_4$—CH—CH$_2$ (epoxide) | D-257 |
| 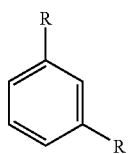 | R = 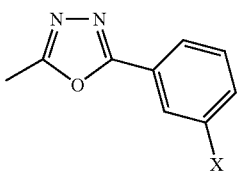 | X = —COOC$_4$H$_9$ | D-258 |
| | | —COOC$_5$H$_{11}$ | D-259 |
| | | —COOC$_6$H$_{13}$ | D-260 |
| | | —COO(CH$_2$)$_2$OCOCH=CH$_2$ | D-261 |
| | | —COO(CH$_2$)$_3$OCOCH=CH$_2$ | D-262 |
| | | —COO(CH$_2$)$_4$OCOCH=CH$_2$ | D-263 |
| | | —COO(CH$_2$)$_5$OCOCH=CH$_2$ | D-264 |
| | | —COO(CH$_2$)$_6$OCOCH=CH$_2$ | D-265 |
| | | —COO(CH$_2$)$_7$OCOCH=CH$_2$ | D-266 |
| | | —COO(CH$_2$)$_8$OCOCH=CH$_2$ | D-267 |
| | | —COO(CH$_2$CH$_2$O)$_2$COCH=CH$_2$ | D-268 |
| | | —COO(CH$_2$)$_2$CH(CH$_3$)OCOCH=CH$_2$ | D-269 |
| | | —COO(CH$_2$)$_3$CH(CH$_3$)OCOCH=CH$_2$ | D-270 |
| | | —COO(CH$_2$)$_4$CH(CH$_3$)OCOCH=CH$_2$ | D-271 |
| | | —COOCH$_2$CH(CH$_3$)CH$_2$OCOCH=CH$_2$ | D-272 |
| | | —COO(CH$_2$)$_2$CH(CH$_3$)(CH$_2$)$_2$OCOCH=CH$_2$ | D-273 |
| | | —COOCH(CH$_3$)(CH$_2$)$_2$OCOCH=CH$_2$ | D-274 |
| | | —COO(CH$_2$)$_5$OCOC(CH$_3$)=CH$_2$ | D-275 |
| | | —COO(CH$_2$)$_4$OCH=CH$_2$ | D-276 |
| | | —COO(CH$_2$)$_4$—CH—CH$_2$ (epoxide) | D-277 |

Compounds of formula (I), formula (II) and formula (III) can be readily produced according to ordinary methods of producing organic synthetic compounds. For example, they may be readily produced by suitably selecting and combining the methods described in Organic Synthesis, Organic Reactions, Lecture of Experimental Chemistry (by Maruzen Publishing). Aromatic hetero rings may be produced according to the description given in Heterocyclic Compounds, New Edition, Applications (by Kodansha Scientific). Regarding 1,2,4-oxadiazole ring-having compounds, methods of producing compounds similar to them are given in Journal of Medicinal Chemistry, 1972, Vol. 15, pp. 1198-1200 and in Chemische Berichte, 1965, Vol. 98, pp. 2966-2984, and they may be produced according to the methods.

"Uniformly aligned state" in the invention is meant to indicate a uniform monodomain alignment state with no defect. For realizing the alignment state, desired is a liquid-crystal phase capable of expressing good monodomain performance. When the monodomain performance of molecules is poor, then the structure that the molecules form exhibits polydomain performance, therefore having alignment defects in the boundary between domains and scattering light. When the molecules have good monodomain performance, and when they are used, for example, in a retardation plate, then the retardation plate may readily have good light transmittance.

Preferably, the compound of formula (I) expresses an $N_D$ phase with a range of from 20° C. to 300° C., more preferably within a range of from 40° C. to 280° C., even more preferably within a range of from 60° C. to 250° C. The wording "expressing a liquid-crystal phase within a range of from 20° C. to 300° C." as referred to herein means that the liquid-crystal temperature range of the compound covers nearly 20° C. (for example, from 10° C. to 22° C.) and nearly 300° C. (for example, from 298° C. to 310° C.). The same shall apply to the range of from 40° C. to 280° C., and to the range of from 60° C. to 250° C.

For obtaining uniformly-aligned thin films in the invention, for example, any other additive is optionally added to the $N_D$ material of the invention to give a composition (liquid-crystal composition), and the composition may be applied onto a substrate to form a film in which the molecules are uniformly aligned when they are in a liquid-crystal state. Examples of the additive that maybe added to the composition of the invention are an air-interface alignment controlling agent, a repelling inhibitor, a polymerization initiator, a polymerizable monomer.

The alignment state of the compound of formula (I) is preferably homeotropic alignment, hybrid alignment or vertical alignment.

The thickness of the thin film in which the composition of the invention is uniformly aligned is preferably from 0.2 to 10.0 µm, more preferably from 0.4 to 4.0 µm.

For realizing a uniformly aligned state of the composition, it is desirable to provide an alignment film. However, when the optical axis direction of the compound of formula (I) corresponds to the normal direction of the face of the thin film containing the compound (in homeotropic alignment), then the alignment film is not always necessary.

The alignment film may be formed, for example, through rubbing treatment of an organic compound (preferably polymer), oblique vapor deposition of an inorganic compound, formation of a microgrooved layer, or accumulation of an organic compound (e.g., ω-tricosanoic acid, methyl stearate) according to a Langmuir-Blodgett's method (LB film). Further, there are known other alignment films that may have an alignment function through impartation of an electric field or magnetic field thereto or through light irradiation thereto.

The alignment film may be any one capable of imparting the desired alignment to the composition of the invention. Preferably, in the invention, the alignment film is formed through rubbing treatment or light irradiation. More preferably, it is formed through rubbing treatment of polymer. Rubbing treatment may be generally attained by rubbing the surface of a polymer layer a few times with paper or cloth in a predetermined direction. Preferably in the invention, the methods described in Handbook of Liquid Crystals (by Maruzen) are employed. Preferably, the thickness of the alignment film is from 0.01 to 10 µm, more preferably from 0.05 to 3 µm.

Rubbing Density of Alignment Film:

Regarding the relation between the rubbing density of an alignment film and the pretilt angle of the compound of formula (I) in the interface of the alignment film, the pretilt angle becomes smaller when the rubbing density is larger, but the pretilt angle becomes larger when the rubbing density is smaller. Accordingly, the pretilt angle of the compound can be controlled by changing the rubbing density of the alignment film.

For changing the rubbing density of an alignment film, for example, employable are the methods described in Handbook of Liquid Crystals, edited by the Society of Editing Handbook of Liquid Crystals (by Maruzen 2000). The rubbing density (L) is quantified by the following formula (A):

$$L=Nl\{1+(2\pi rn/60v)\} \tag{A}$$

wherein N represents the number of rubbing frequency; l represents the contact length of a rubbing roller; r represents the radius of the roller; n represents the number of roller revolution (rpm); v represents a stage moving speed (per second). For increasing the rubbing density, for example, the number of rubbing frequency may be increased, or the contact length of the rubbing roller may be prolonged, or the radium of the roller may be increased, or the number of roller revolution may be increased, or the stage moving speed may be lowered. On the other hand, for lowering the rubbing density, the opposite of the above may be attained.

One typical and preferred embodiment of the "fixed alignment state" as referred to herein is that the alignment state of liquid crystal is fixed, which, however, is not limitative. For example, the state in question should include a case where the fixed composition may lose or has lost flowability within a temperature range of from 0° C. to 50° C., or within a temperature range of from −30° C. to 70° C. under a severer condition, and the alignment state is not changed at all by any external field or external force applied thereto, and the thus-fixed alignment state can be stably kept as it is. In an optically-anisotropic layer in which the alignment state of molecules is finally fixed, the composition of the invention is no more required to exhibit liquid crystallinity. For example, when the liquid-crystal compound of formula (I) has a polymerizable group, it may be finally polymerized or crosslinked by exposure to heat or light to thereby have an increased molecular weight, and may finally lose its liquid crystallinity.

Examples of the additive that may be added to the composition of the invention in forming an optically-anisotropic layer are an air-interface alignment-controlling agent, a repelling inhibitor, a polymerization initiator, and a polymerizable monomer.

Air-Interface Alignment-Controlling Agent:

In an air interface, the composition of the invention is aligned at a tilt angle to the air interface. The tilt angle varies depending on the type of the compound and the type of the additive in the composition of the invention, and therefore, the tilt angle of the composition to an air interface must be controlled in any desired manner depending on the object of the composition.

For controlling the tilt angle, for example, an external field such as an electric field or a magnetic field may be applied to the composition, or an additive may be added to the composition. Preferably, an additive is added to the composition. The additive is preferably a compound having, in the molecule, at least one of a substituted or unsubstituted aliphatic group having from 6 to 40 carbon atoms or a substituted or unsubstituted aliphatic oligosiloxanoxy group having from 6 to 40 carbon atoms, more preferably at least two of such groups. For example, as an air-interface alignment-controlling agent for that purpose, herein employable are hydrophilic, excluded volume effect compounds as in JP-A-2002-20363.

The amount of the alignment-controlling agent to be added to the air interface side is preferably from 0.001 to 20% by mass of the composition of the invention, more preferably from 0.01% by mass to 10% by mass, even more preferably from 0.1% by mass to 5% by mass.

Repelling Inhibitor:

As a material that may be added to the composition of the invention for preventing the composition from being repelled in its application to subjects, generally preferred are polymer compounds.

The polymer to be used for that purpose is not specifically defined, not significantly interfering with the tilt angle change and the alignment of the composition of the invention.

Examples of the polymer are described in JP-A-8-95030. Especially preferred examples of the polymer are cellulose esters. Examples of the cellulose esters are cellulose acetate, cellulose acetate propionate, hydroxypropylcellulose and cellulose acetate butyrate.

The amount of the polymer that may be added to the composition of the invention not detracting from the alignment of the composition is preferably from 0.1 to 10% by mass, more preferably from 0.1 to 8% by mass, even more preferably from 0.1 to 5% by mass.

Polymerization Initiator:

For fixing the alignment state of liquid-crystal molecules in the invention, the composition of the invention may be heated up to a liquid-crystal phase-forming temperature thereof, and then cooled while its alignment state is kept as such, whereby the composition may be fixed as such not detracting from the alignment state of the liquid-crystal condition of the composition. When a polymerization initiator is added to the composition of the invention and when the composition is heated up to its liquid-crystal phase-forming temperature and thereafter polymerized and cooled, then the alignment state of the liquid-crystal condition of the composition may be fixed as such. In the invention, the fixation of the alignment state is preferably attained through the latter polymerization mode. The polymerization includes thermal polymerization with a thermal polymerization initiator, optical polymerization with an optical polymerization initiator, and polymerization by irradiation with electron rays. For preventing the support and others from being deformed and degraded by heat, preferred is optical polymerization or polymerization by irradiation with electron rays.

Examples of the optical polymerization initiator are α-carbonyl compounds (as in U.S. Pat. Nos. 2,367,661, 2,367,670), acyloin ethers (as in U.S. Pat. No. 2,448,828), α-hydrocarbon-substituted aromatic acyloin compounds (as in U.S. Pat. No. 2,722,512), polynuclear quinone compounds (as in U.S. Pat. Nos. 3,046,127, 2,951,758), combination of triarylimidazole dimer and p-aminophenyl ketone (as in U.S. Pat. No. 3,549,367), combination of acridine and phenazine compound (as in JP-A-60-105667, U.S. Pat. No. 4,239,850), and oxadiazole compounds (as in U.S. Pat. No. 4,212,970).

The amount of the optical polymerization initiator to be added to the composition is preferably from 0.01 to 20% by mass of the solid content of the coating liquid for optically-anisotropic layer, more preferably from 0.5 to 5% by mass.

For light irradiation for polymerization, preferably used are UV rays. The irradiation energy is preferably from 10 mJ/cm$^2$ to 50 J/cm$^2$, more preferably from 50 mJ/cm$^2$ to 800 mJ/cm$^2$. For promoting optical polymerization, the light irradiation may be effected under heat. Since the oxygen concentration in the atmosphere participates in the degree of polymerization of the composition, it is desirable that the oxygen concentration is lowered by nitrogen purging or the like when the degree of polymerization of the processed composition could not reach the desired level in air. Preferably, the oxygen concentration is at most 10%, more preferably at most 7%, even more preferably at most 3%.

Polymerizable Monomer:

A polymerizable monomer may be added to the composition of the invention. Not specifically defined, the polymerizable monomer usable in the invention may be any one compatible with the compound of formula (I) not causing significant failure in alignment of the composition of the invention. Preferred is a compound having a polymerization-active ethylenic unsaturated group, such as a vinyl group, a vinyloxy group, an acryloyl group or a methacryloyl group. The amount of the polymerizable monomer that may be added to the composition of the invention is preferably from 0.5 to 50% by mass of the compound of formula (I) in the composition, more preferably from 1 to 30% by mass. When a monomer having 2 or more reactive functional groups is used, then an effect of improving the adhesiveness between the alignment film and the optically-anisotropic layer may be expected, and the monomer of the type is especially preferred.

Coating Solvent:

The solvent to be used in preparing the composition of the invention is preferably an organic solvent. Preferred examples of the organic solvent are amides (e.g., N,N-dimethylformamide), sulfoxides (e.g., dimethylsulfoxide), heterocyclic compounds (e.g., pyridine), hydrocarbons (e.g., toluene, hexane), alkyl halides (e.g., chloroform, dichloromethane), esters (e.g., methyl acetate, butyl acetate), ketones (e.g., acetone, methyl ethyl ketone, methyl isobutyl ketone, cyclohexanone), ethers (e.g., tetrahydrofuran, 1,2-dimethoxyethane). Preferred are alkyl halides, esters and ketones. Two or more different types of such organic solvents may be used herein, as combined.

Coating Method:

For example, the composition of the invention may be applied onto an alignment film and aligned to give an optical film.

The coating liquid may be applied in any known method (for example, spin coating, wire bar coating, extrusion coating, direct gravure coating, reverse gravure coating, die coating).

Retardation Plate:

The retardation plate of the invention has an optically-anisotropic layer formed with the composition of the invention, on a transparent support. Preferably, an alignment film is provided between the transparent support and the optically-anisotropic layer. The optically-anisotropic layer may be formed, for example, by optionally adding an additive to the composition of the invention, then applying the resulting composition onto an alignment film, and thereafter fixing the alignment of the liquid-crystal state of the composition.

Preferably, the thickness of the optically-anisotropic layer in the retardation plate of the invention is from 0.1 to 20 µm, more preferably from 0.2 to 15 µm, even more preferably from 0.5 to 10 µm.

The retardation plate of the invention may be combined with a polarizing film for use for elliptically-polarizing plates. As combined with a polarizing film, the retardation plate may also be used in transmission-type, reflection-type and semi-transmission-type liquid-crystal display devices, in which the plate may contribute toward enlarging the viewing angle of the devices.

Support:

Not specifically defined, the support of the retardation plate of the invention is preferably a transparent support. After the above optically-anisotropic layer has been formed on a temporary support, the optically-anisotropic layer alone may be transferred onto a different support to produce the retardation plate of the invention. Not specifically defined, the material of the transparent support may be any one that is essentially optically isotropic and has a light transmittance of at least 80%. Preferably, however, the support is a polymer film.

Examples of the polymer are cellulose esters (e.g., cellulose diacetate, cellulose triacetate), norbornene polymers, poly(meth)acrylates. Many commercially-available polymers may be favorably used for the support. Of those, more preferred are cellulose esters in view of the optical properties thereof; even more preferred are lower fatty acid esters of cellulose. The lower fatty acid is a fatty acid having at most 6 carbon atoms, preferably having 2 (cellulose acetate), 3 (cellulose propionate) or 4 (cellulose butyrate) carbon atoms. Especially preferred is cellulose triacetate. A mixed fatty acid ester such as cellulose acetate propionate, cellulose acetate butyrate may also be used. Conventional polymers that may readily express birefringence, such as polycarbonates or polysulfones are also usable herein so far as they are modified according to molecule modification as in WO00/26705 to thereby lower their ability to express birefringence.

Cellulose acylate (especially cellulose triacetate) preferred for use as the transparent support in the invention is described in detail hereinunder.

Cellulose acylate for support is preferably cellulose acetate having a degree of acetylation of from 55.0 to 62.5%, more preferably from 57.0 to 62.0%. The degree of acetylation as referred to herein means the amount of the bonding acetic acid per cellulose unit mass. The degree of acetylation may be determined according to determination and computation in ASTM D-817-91 (method for testing cellulose acetate, etc.). Preferably, the viscosity-average degree of polymerization (DP) of the cellulose ester is at least 250, more preferably at least 290. Preferably, the molecular weight distribution, Mw/Mn by gel permeation chromatography (Mw is a mass-average molecular weight, and Mn is a number-average molecular weight) of the cellulose ester for use in the invention is narrow. Concretely, Mw/Mn of the ester is preferably from 1.0 to 1.7, more preferably from 1.3 to 1.65, even more preferably from 1.4 to 1.6.

In cellulose acylate, the overall degree of substitution is not always uniformly divided into 3 for the degree of substitution at the 2-, 3- and 6-positioned hydroxyl groups of cellulose to be ⅓ each, but the degree of substitution at the 6-positioned hydroxyl group tends to be small. In the invention, however, the degree of substitution at the 6-positioned hydroxyl group of cellulose is preferably higher than that at the 2- and 3-positioned hydroxyl groups thereof. Preferably, the degree of substitution at the 6-positioned hydroxyl group is from 30% to 40% of the overall degree of substitution, more preferably from 31 to 40%, even more preferably from 32 to 40%.

Preferably, the degree of substitution at the 6-position is at least 0.88. The 6-positioned hydroxyl group may be substituted with any other acyl group having 3 or more carbon atoms (e.g., propionyl group, butyryl group, valeroyl group, benzoyl group, acryloyl group), apart from with an acetyl group. The degree of substitution at each position may be determined through NMR. Cellulose ester having a high degree of substitution at the 6-positioned hydroxyl group may be produced with reference to JP-A11-5851, concretely, the method of Production Example 1 in paragraphs [0043] to [0044], Production Example 2 in paragraphs [0048] to [0049] and Production Example 3 in paragraphs [0051] to [0052].

The polymer film, especially the cellulose acylate film for the transparent support may contain an aromatic compound having at least two aromatic groups and serving as a retardation improver for the purpose of controlling the retardation value of the film. When such a retardation improver is added to the film, then its amount is preferably from 0.01 to 20 parts by mass, more preferably from 0.05 to 15 parts by mass, even more preferably from 0.1 to 10 parts by mass, relative to 100 parts by mass of cellulose acylate. Two or more aromatic compounds may be combined and used for the retardation improver.

The aromatic ring of the aromatic compound as referred to herein is meant to include not only aromatic hydrocarbon rings but also aromatic hetero rings.

The aromatic hydrocarbon ring is preferably a 6-membered ring (that is, benzene ring).

The aromatic hetero ring is generally an unsaturated hetero ring. The aromatic hetero ring is preferably a 5-membered, 6-membered or 7-membered ring, more preferably a 5-membered or 6-membered ring. The aromatic hetero ring generally has a largest number of double bonds. The hetero atom of the ring is preferably a nitrogen atom, an oxygen atom and a sulfur atom, more preferably a nitrogen atom.

The aromatic ring is preferably a benzene ring, a furan ring, a thiophene ring, a pyrrole ring, an oxazole ring, a thiazole ring, an imidazole ring, a triazole ring, a pyridine ring, a pyrimidine ring, a pyrazine ring and a 1,3,5-triazine ring, more preferably a benzene ring and a 1,3,5-triazine ring. Especially preferably, the aromatic compound has at least one 1,3,5-triazine ring.

Examples of the aromatic hetero ring are a furan ring, a thiophene ring, a pyrrole ring, an oxazole ring, an isoxazole ring, a thiazole ring, an isothiazole ring, an imidazole ring, a pyrazole ring, a furazan ring, a triazole ring, a pyran ring, a pyridine ring, a pyridazine ring, a pyrimidine ring, a pyrazine ring and a 1,3,5-triazine ring.

The number of the aromatic rings that the aromatic compound has is preferably from 2 to 20, more preferably from 2 to 12, even more preferably from 2 to 8, still more preferably from 2 to 6. The bonding relation between two aromatic rings in the compound may be grouped into (a) a case where the two rings form a condensed ring, (b) a case where the two rings bond to each other via a single bond, and (c) a case where the two rings bond to each other via a linking group (in this, since the rings are aromatic rings, they could not form a spiro bond) In the invention, the bonding relation may be any of (a) to (c). The retardation improver of the type is described in WO01/88574A1, WO00/2619A1, JP-A-2000-111914, JP-A-2000-275434, JP-A-2002-363343.

The cellulose acylate film for use herein is preferably produced from a prepared cellulose acylate solution (dope) according to a solvent-casting process. The above-mentioned retardation improver may be added to the dope.

The dope is cast on a drum or a band, on which the solvent is evaporated away to form a film. Before cast, the concentration of the dope is preferably so controlled that the solid content thereof is from 18 to 35%. Preferably, the surface of the drum or the band is finished to have a mirror face. The casting and drying method in the solvent-casting process is described in U.S. Pat. Nos. 2,336,310, 2,367,603, 2,492,078, 2,492,977, 2,492,978, 2,607,704, 2,739,069, 2,739,070; British Patent 640731, British Patent 736892; JP-B-49-4554, JP-B-49-5614; JP-A-60-176834, JP-A-60-203430, JP-A-62-115035.

Preferably, the dope is cast onto a drum or a band having a surface temperature of at most 10° C. Preferably, the cast dope is dried through exposure to air for at least 2 seconds. The formed film is peeled away from the drum or band, and it may be further dried with hot air of which the temperature is successively changed up to 100 to 160° C., thereby evaporating away the remaining solvent. This method is described in JP-A-5-17844. According to the method, the time to be taken from casting to peeling may be shortened. To be processed according to the method, the dope must gel at the surface temperature of the drum or band on which it is cast.

The prepared cellulose acylate solutions (dopes) may be cast into two or more layers to form a film. The dope may be cast onto a drum or a band, on which the solvent may be evaporated away to give a film. Before cast, the concentration of the dope is preferably so controlled that the solid content thereof could be from 10 to 40%. Preferably, the surface of the drum or the band is finished to have a mirror face.

In case where plural cellulose acylate solutions are cast, the cellulose acylate-containing solutions may be separately cast from the respective casting ports disposed at intervals in the machine direction in which the support travels, and laminated into a multi-layered film. For example, the methods described in JP-A-61-158414, JP-A-1-122419, JP-A-11-198285 may be employed. Cellulose acetate solutions may be cast through two casting ports, thereby forming a film. For example, the methods described in JP-B-60-27562, JP-A-61-94724, JP-A-61-104813, JP-A-61-158413, JP-A-6-134933 may be employed. In addition, the method described in JP-A-56-162617 is also employable herein, which is a casting method for producing a cellulose acetate film and comprises enveloping a flow of a high-viscosity cellulose acetate solution in a low-viscosity cellulose acetate solution and simultaneously extruding the high-density and low-density cellulose acetate solutions.

The retardation of the cellulose acetate film may be controlled by stretching the film. Preferably, the draw ratio in stretching the film is from 0 to 100%. The cellulose acylate film for use in the invention is stretched preferably with a tenter. Preferably, for accurately controlling the slow axis of the stretched film, the difference in the tenter clip speed and the release timing between the left clip and the right clip is as small as possible.

A plasticizer may be added to the cellulose acylate film for improving the physical properties of the film and for improving the driability of the film. Phosphates or carboxylates may be used for the plasticizer. Examples of the phosphates are triphenyl phosphate (TPP), diphenylbiphenyl phosphate and tricresyl phosphate (TCP). The carboxylates are typically phthalates and citrates. Examples of the phthalates are dimethyl phthalate (DMP), diethyl phthalate (DEP), dibutyl phthalate (DBP), dioctyl phthalate (DOP), diphenyl phthalate (DPP) and di-2-ethylhexyl phthalate (DEHP). Examples of the citrates are triethyl o-acetylcitrate (OACTE) and tributyl o-acetylcitrate (OACTB). Examples of the other carboxylates are butyl oleate, methylacetyl ricinoleate, dibutyl sebacate, and various trimellitates. Preferred are phthalate plasticizers (DMP, DEP, DBP, DOP, DPP, DEHP). The amount of the plasticizer to be added is preferably from 0.1 to 25% by mass of the amount of cellulose ester, more preferably from 1 to 20% by mass, even more preferably from 3 to 15% by mass.

A degradation inhibitor (e.g., antioxidant, peroxide-decomposing agent, radical inhibitor, metal inactivator, acid scavenger, amine) and a UV inhibitor may be added to the cellulose acylate film. The degradation inhibitor is described in JP-A-3-199201, JP-A-5-197073, JP-A-5-194789, JP-A-5-271471, JP-A-6-107854. The amount of the degradation inhibitor to be added is preferably from 0.01 to 1% by mass of the prepared solution (dope), more preferably from 0.01 to 0.2% by mass. When the amount thereof is at least 0.01% by mass, then the degradation inhibitor could be more effective. When the amount thereof is at most 0.2% by mass, then the degradation inhibitor may be more effectively prevented from bleeding out on the film surface.

Especially preferably, the degradation inhibitor is butylated hydroxytoluene (BHT). The UV inhibitor is described in JP-A-7-11056.

Preferably, the cellulose acylate film is surface-treated. Concretely, the surface treatment includes corona discharge treatment, glow discharge treatment, flame treatment, acid treatment, alkali treatment, UV irradiation treatment. As in JP-A-7-333433, it may be desirable to form an undercoat layer on the film.

From the viewpoint of keeping the surface smoothness thereof, the temperature of the cellulose acylate film in the surface treatment is preferably not higher than the glass transition temperature (Tg) of the film, concretely not higher than 150° C.

From the viewpoint of the adhesiveness thereof to alignment film, the surface treatment of the cellulose acylate film is preferably acid treatment or alkali treatment for saponification of cellulose acylate. An example of alkali saponification treatment is concretely described below. Preferably, alkali saponification comprises a cycle of dipping a film surface in an alkali solution, neutralizing it with an acid solution, washing it and drying it. The alkali solution may be a potassium hydroxide solution or a sodium hydroxide solution. The normality concentration of the hydroxide ion in the solution is preferably from 0.1 to 3.0 mol/L, more preferably from 0.5 to 2.0 mol/L. The temperature of the alkali solution is preferably from room temperature (e.g., 18° C.) to 90° C., more preferably from 40 to 70° C.

Preferably, the surface energy of the cellulose acetate film is at least 55 mN/m, more preferably from 60 to 75 mN/m.

The surface energy may be determined according to a contact angle process, a wet heat process or an absorption process as in Basis and Application of Wetting Technology (by Realize, issued Dec. 10, 1989). A contact angle process is preferred for the cellulose acylate film for use in the invention. Concretely, two solutions of which the surface energy is known are dropped onto a cellulose acylate film, and at the crossing between the surface of the droplet and the surface of the film, the angle formed by the tangent line drawn to the droplet and the film surface and including the angle on the side of the droplet is defined as the contact angle, and the surface energy of the film is thereby computed.

Preferably, the thickness of the cellulose acylate film is from 5 to 500 μm, more preferably from 20 to 250 μm, even more preferably from 30 to 180 μm, still more preferably from 30 to 110 μm.

Elliptically-Polarizing Plate:

An elliptically-polarizing plate may be produced by laminating the retardation plate of the invention and a polarizing film. Comprising the retardation plate of the invention, the elliptically-polarizing plate may be built in a liquid-crystal display device, in which the plate may act to enlarge the viewing angle of the device.

The polarizing plate includes an iodine-based polarizing plate, a dichroic dye-containing polarizing plate and a polyene-based polarizing plate. The iodine-based polarizing plate and the dye-based polarizing plate may be produced generally from polyvinyl alcohol films. The polarization axis of the polarizing film corresponds to the direction vertical to the stretching direction of the film.

The polarizing film is laminated on the side of the optically-anisotropic layer of the retardation plate. Preferably, a transparent protective film is formed on the opposite side to the side of the retardation plate laminated with the polarizing film. The transparent protective film preferably has a light transmittance of at least 80%. The transparent protective is preferably formed of a cellulose ester film, more preferably a triacetyl cellulose film. Preferably, the cellulose ester film is formed according to a solvent-casting process. Preferably, the thickness of the transparent protective film is from 20 to 500 μm, more preferably from 50 to 200 μm.

Liquid-Crystal Display Device:

The retardation plate of the invention contributes toward enlarging the viewing angle of liquid-crystal display devices comprising it. A retardation plate (optical compensatory film) for TN-mode liquid-crystal cells is described in JP-A-6-214116, U.S. Pat. Nos. 5,583,679, 5,646,703, and German Patent 3911620A1. A retardation plate for IPS-mode or FLC-mode liquid-crystal cells is described in JP-A-10-54982. A retardation plate for OCB-mode or HAN-mode liquid-crystal cells is described in U.S. Pat. No. 5,805,253 and WO96/37804. An optical compensatory film for STN-mode liquid-crystal cells is described in JP-A-9-26572. An optical compensatory film for VA-mode liquid-crystal cells is described in Japanese Patent 2866372.

In the invention, retardation plates (optical compensatory sheets) for various modes of liquid-crystal cells as above may be produced with reference to the description of the above-mentioned patent publications. The retardation plate of the invention may be used in various display modes of liquid-crystal display devices, such as TN (twisted nematic)-mode, IPS (in-plane switching)-mode, FLC (ferroelectric liquid-crystal)-mode, OCB (optically-compensatory bent)-mode, STN (super-twisted nematic)-mode, VA (vertically-aligned)-mode and HAN (hybrid aligned nematic)-mode liquid-crystal display devices.

A liquid-crystal display device comprises a liquid-crystal cell, a polarizing element and a retardation plate (optical compensatory film). The polarizing element generally comprises a polarizing film and a protective film, in which the polarizing film and the protective film may be the same as those mentioned for the above elliptically-polarizing plate.

EXAMPLES

The invention is described more concretely with reference to the following Examples. In the following Examples, the material used, its amount and ratio, the details of the treatment and the treatment process may be suitably modified or changed not overstepping the spirit and the scope of the invention. Accordingly, the invention should not be limitatively interpreted by the Examples mentioned below.

Example 1

Production of D-224

This was produced according to the following scheme:

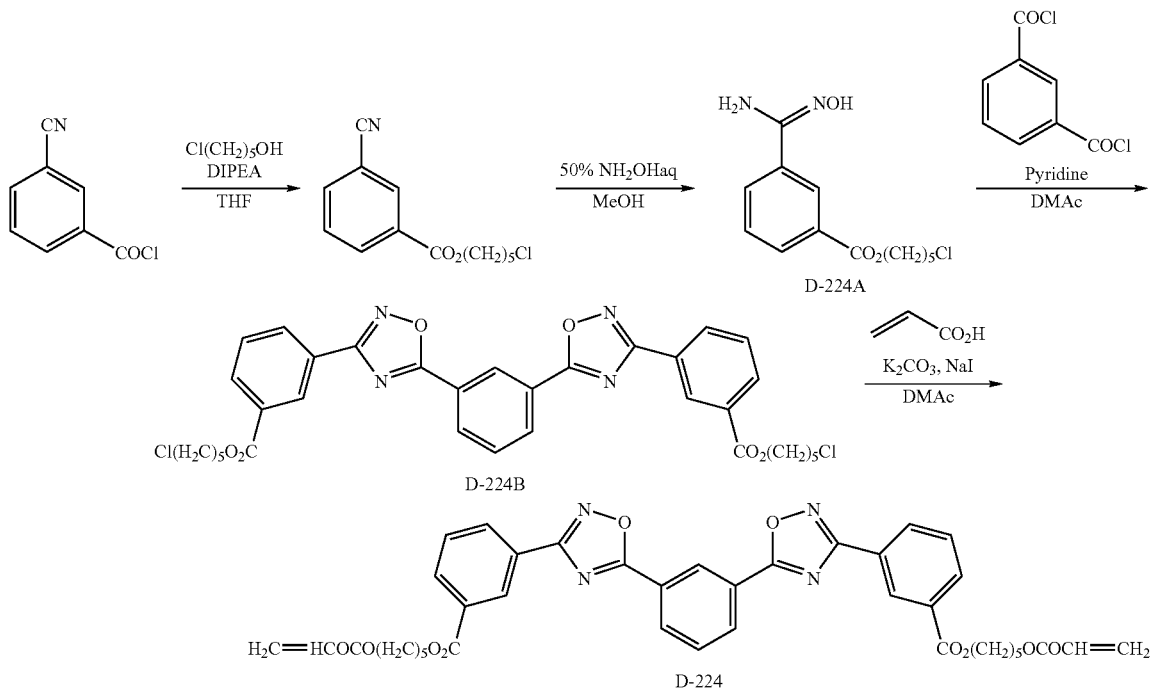

Production of D-224A 2.5 g of 3-cyanobenzoyl chloride was dissolved in 20 ml of tetrahydrofuran (THF), then 1.9 g of 5-chloro-1-pentanol and 3.0 ml of diisopropylethylamine (DIPEA) were added thereto, and stirred at room temperature for 1 hour. Water was added to the reaction liquid, and extracted with ethyl acetate, and the organic layer was concentrated under reduced pressure. The residue was dissolved in 100 ml of methanol (MeOH), then 2.8 ml of 50% hydroxylamine solution was added thereto, and stirred at 40° C. for 1 hour. After cooled, water was added to the reaction liquid, and the precipitated crystal was taken out through filtration and dried to obtain 3.8 g of D-224A.

Production of D-224B 2.8 g of D-224A was dissolved in 10 ml of dimethylacetamide (DMAc), then 0.8 ml of pyridine and 0.8 g of isophthaloyl chloride were added thereto, and stirred at 120° C. for 1 hour. After cooled, methanol was added to it, and the precipitated crystal was taken out through filtration and dried to obtain 2.1 g of D-224B.

Production of D-224

2.1 g of D-224B was dissolved in 30 ml of dimethylacetamide, then 2.7 g of potassium carbonate, 2.9 g of sodium iodide and 1.3 ml of acrylic acid were added thereto, and stirred at 100° C. for 3 hours. Water was added to the reaction liquid, and the precipitated crystal was taken out through filtration. This was purified through column chromatography to obtain 1.8 g of D-224. The NMR spectrum of the thus-obtained D-224 is as follows:

1H-NMR (solvent: CDCl3, standard: tetramethylsilane) δ (ppm): 1.60 (4H, m), 1.80-1.90 (8H, m), 4.20 (4H, t), 4.45 (4H, t), 5.80 (2H, dd), 6.15 (2H, dd), 6.40 (2H, dd), 7.65 (2H, t), 7.80 (1H, t), 8.25 (2H, d), 8.40 (2H, d), 8.50 (2H, d), 8.90 (2H, s), 9.10 (1H, s)

The phase transition temperature of D-224 was determined through texture observation with a polarizing microscope. While heated, this changed from a crystal phase to a discotic nematic liquid-crystal phase at around 72° C., and then further changed to an isotropic liquid phase at higher than 75° C. Accordingly, it was confirmed that D-224 expresses a discotic nematic liquid-crystal phase between 72° C. and 75° C.

Example 2

Production of D-223

This was produced according to the following scheme:

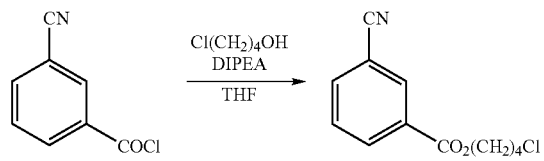
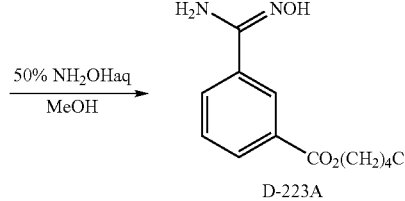
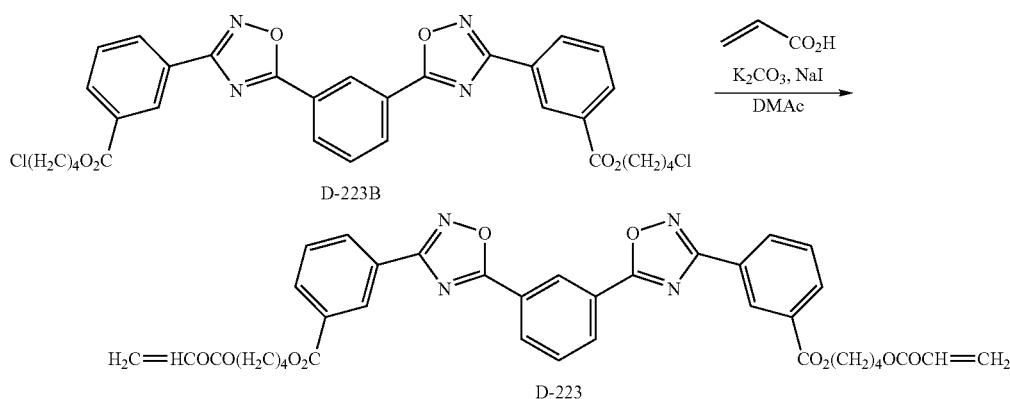

2.0 g of D-223 was obtained in the same manner as in Example 1, for which, however, 4-chloro-1-butanol was used in place of 5-chloro-1-pentanol. The NMR spectrum of the thus-obtained D-223 is as follows:

1H-NMR (solvent: CDCl3, standard: tetramethylsilane) δ (ppm): 1.85-2.00 (8H, m), 4.30 (4H, t), 4.45 (4H, t), 5.85 (2H, dd), 6.15 (2H, dd), 6.40 (2H, dd), 7.65 (2H, t), 7.80 (1H, t), 8.25 (2H, d), 8.40 (2H, d), 8.50 (2H, d), 8.90 (2H, s), 9.10 (1H, s)

The phase transition temperature of D-223 was determined through texture observation with a polarizing microscope. While heated, this changed from a crystal phase to a discotic nematic liquid-crystal phase at around 74° C., and then further changed to an isotropic liquid phase at higher than 90° C. Accordingly, it was confirmed that D-223 expresses a discotic nematic liquid-crystal phase between 74° C. and 90° C.

Example 3

Production of D-222

This was produced according to the following scheme:

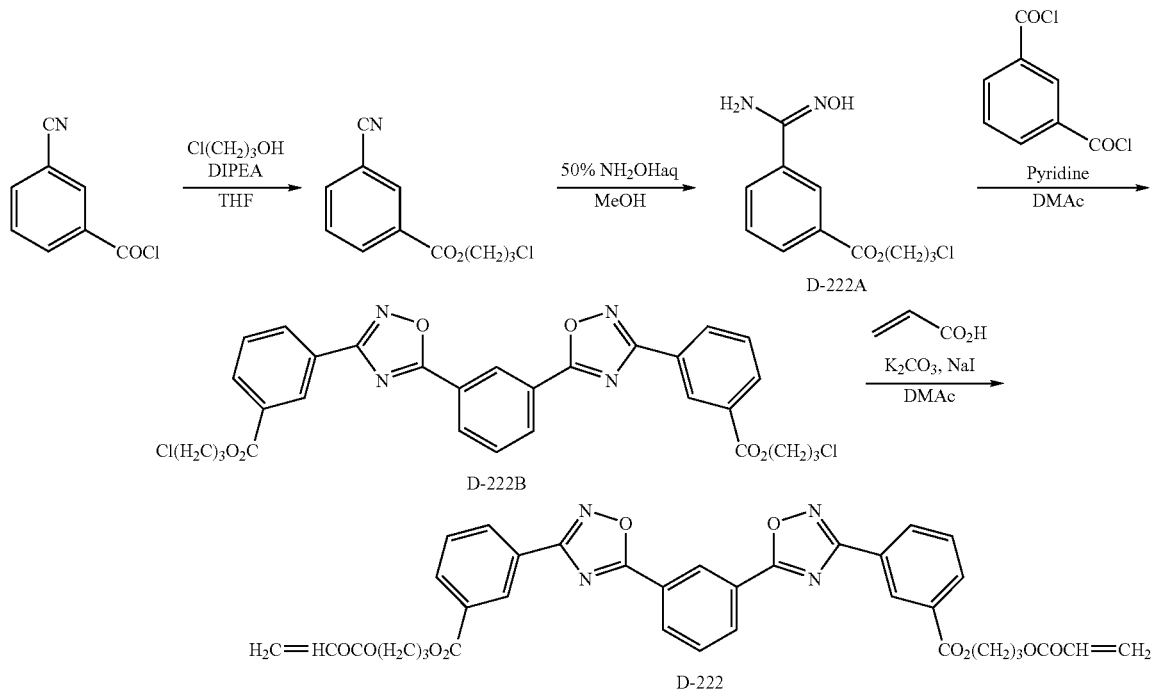

1.2 g of D-222 was obtained in the same manner as in Example 1, for which, however, 3-chloro-1-propanol was used in place of 5-chloro-1-pentanol. The NMR spectrum of the thus-obtained D-222 is as follows:

1H-NMR (solvent: CDCl3, standard: tetramethylsilane) δ (ppm): 2.20 (4H, quint), 4.40 (4H, t), 4.50 (4H, t), 5.80 (2H, dd), 6.10 (2H, dd), 6.40 (2H, dd), 7.65 (2H, t), 7.80 (1H, t), 8.20 (2H, d), 8.40 (2H, d), 8.45 (2H, d), 8.85 (2H, s), 9.10 (1H, s)

The phase transition temperature of D-222 was determined through texture observation with a polarizing microscope. While heated, this changed from a crystal phase to a discotic nematic liquid-crystal phase at around 94° C., and then further changed to an isotropic liquid phase at higher than 97° C. Accordingly, it was confirmed that D-222 expresses a discotic nematic liquid-crystal phase between 94° C. and 97° C.

Example 4

Production of D-221

This was produced according to the following scheme:

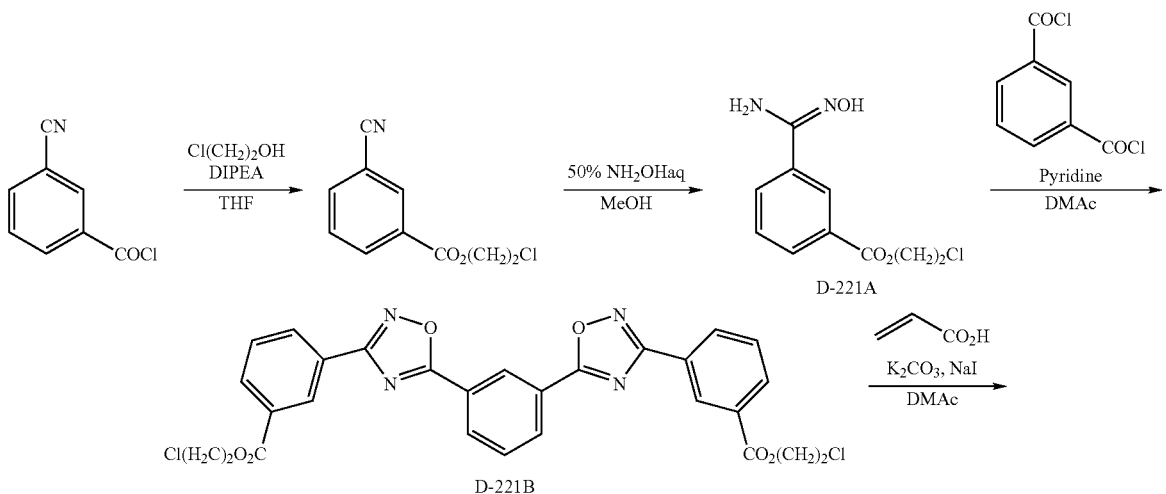

-continued

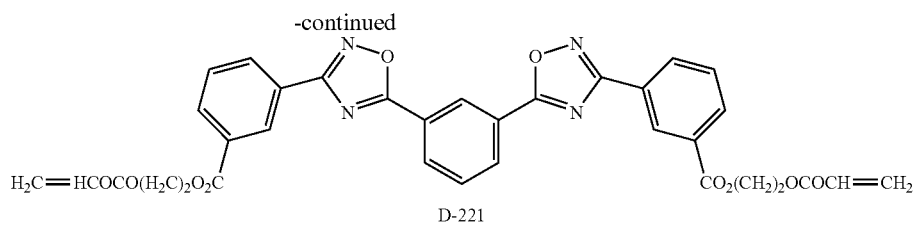

D-221

0.8 g of D-221 was obtained in the same manner as in Example 1, for which, however, 2-chloroethanol was used in place of 5-chloro-1-pentanol. The NMR spectrum of the thus-obtained D-221 is as follows:

1H-NMR (solvent: CDCl3, standard: tetramethylsilane) δ (ppm): 4.55 (4H, t), 4.65 (4H, t), 5.85 (2H, dd), 6.15 (2H, dd), 6.50 (2H, dd), 7.65 (2H, t), 7.80 (1H, t), 8.20 (2H, d), 8.40 (2H, d), 8.45 (2H, d), 8.85 (2H, s), 9.10 (1H, s)

The phase transition temperature of D-221 was determined through texture observation with a polarizing microscope. While heated, this changed from a crystal phase to a discotic nematic liquid-crystal phase at around 90° C., and then further changed to an isotropic liquid phase at higher than 112° C. Accordingly, it was confirmed that D-221 expresses a discotic nematic liquid-crystal phase between 90° C. and 112° C.

The invention claimed is:

1. A discotic nematic material comprising a compound of the following formula (II):

Formula (II)

wherein $Y^{11}$ and $Y^{12}$ each independently represents the following formula (II-A), (II-B) or (II-C):

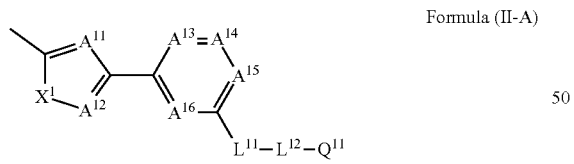

Formula (II-A)

wherein $A^{11}$, $A^{12}$, $A^{13}$, $A^{14}$, $A^{15}$ and $A^{16}$ each independently represents a methine group or a nitrogen atom; $X^1$ represents an oxygen atom, a sulfur atom, a methylene group or an imino group; $L^{11}$ represents —O—, —O—CO—, —CO—O—, —O—CO—O—, —S—, —NH—, —SO$_2$—, —CH$_2$—, —CH=CH— or —C≡C—, $L^{12}$ represents a divalent linking group selected from —O—, —S—, —C(=O)—, —SO$_2$—, —NH—, —CH$_2$—, —CH=CH— and —C≡C—, and their combinations, and when the group has a hydrogen atom, the hydrogen atom may be substituted with a substituent; $Q^{11}$ represents a polymerizable group or a hydrogen atom;

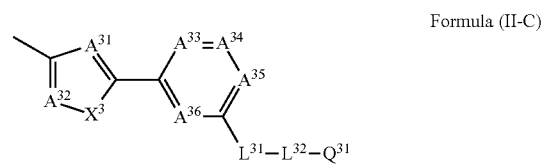

Formula (II-B)

wherein $A^{21}$, $A^{22}$, $A^{23}$, $A^{24}$, $A^{25}$ and $A^{26}$ each independently represents a methine group or a nitrogen atom; $X^2$ represents an oxygen atom, a sulfur atom, a methylene group or an imino group; $L^{21}$ represents —O—, —O—CO—, —CO—O—, —O—CO—O—, —S—, —NH—, —SO$_2$—, —CH$_2$—, —CH=CH— or —C≡C—, $L^{22}$ represents a divalent linking group selected from —O—, —S—, —C(=O)—, —SO$_2$—, —NH—, —CH$_2$—, —CH=CH— and —C≡C—, and their combinations, and when the group has a hydrogen atom, the hydrogen atom may be substituted with a substituent; $Q^{21}$ represents a polymerizable group or a hydrogen atom;

Formula (II-C)

wherein $A^{31}$, $A^{32}$, $A^{33}$, $A^{34}$, $A^{35}$ and $A^{36}$ each independently represents a methine group or a nitrogen atom; $X^3$ represents an oxygen atom, a sulfur atom, a methylene group or an imino group; $L^{31}$ represents —O—, —O—CO—, —CO—O—, —O—CO—O—, —S—, —NH—, —SO$_2$—, —CH$_2$—, —CH=CH— or —C≡C—, $L^{32}$ represents a divalent linking group selected from —O—, —S—, —C(=O)—, —SO$_2$—, —NH—, —CH$_2$, —CH=CH— and —C≡C—, and their combinations, and when the group has a hydrogen atom, the hydrogen atom may be substituted with a substituent; $Q^{31}$ represents a polymerizable group or a hydrogen atom.

2. The discotic nematic material according to claim 1, wherein the ring containing $X^1$, $A^{11}$, and $A^{12}$ in Formula (II-A) and the ring containing $X^3$, $A^{31}$, and $A^{32}$ in Formula (II-C) represents a 1,2,4-oxadiazole ring or a 1,2,4-thiadiazole ring and wherein the ring containing $X^2$, $A^{21}$, and $A^{22}$ in Formula (II-B) represents a 1,3,4-oxadiazole ring or a 1,3,4-thiadiazole ring.

3. The discotic nematic material according to claim 2, wherein the ring containing $X^1$, $A^{11}$, and $A^{12}$ in Formula (II-A) and the ring containing $X^3$, $A^{31}$, and $A^{32}$ in Formula (II-C) represents a 1,2,4-oxadiazole ring.

4. A composition comprising a discotic nematic material of claim 1.

5. A retardation plate comprising at least one optically-anisotropic layer on a support, wherein the optically-anisotropic layer is formed with a composition of claim 4.

6. An elliptically-polarizing plate comprising a retardation plate of claim 5 and a polarizing film.

7. A liquid-crystal display device comprising a retardation plate of claim 5.

8. A compound of the following formula (III):

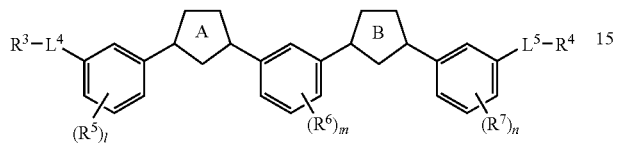

Formula (III)

wherein $R^3$ and $R^4$ each independently represents a linear or branched alkyl group having from 1 to 15 carbon atoms, an alkenyl group having from 2 to 15 carbon atoms, or an alkynyl group having from 2 to 15 carbon atoms, and the hydrogen atom in these groups may be substituted with a substituent; $R^5$, $R^6$ and $R^7$ each independently represents a substituent; I, m and n each independently indicates an integer of from 0 to 4; $L^4$ and $L^5$ each independently represents a single bond or a divalent linking group selected from —O—, —S—, —C(=O)—, —SO$_2$— and —NH— and their combinations; ring A and ring B each independently represents a 1,2,4-oxadiazole-3,5-diyl group, a 1,3,4-oxadiazole-2,5-diyl group, a 1,2,4-thiadiazole-3,5-diyl group, or a 1,3,4-thiadiazole-2,5-diyl group.

9. The compound of claim 8, wherein the ring A and the ring B in formula (III) are a 1,2,4-oxadiazole-3,5-diyl group.

* * * * *